US008262853B2

(12) United States Patent
Holtzapple et al.

(10) Patent No.: US 8,262,853 B2
(45) Date of Patent: Sep. 11, 2012

(54) METHODS FOR PRETREATMENT AND PROCESSING OF BIOMASS

(75) Inventors: Mark Thomas Holtzapple, College Station, TX (US); Richard Read Davison, Bryan, TX (US); Lee Leon Lowery, Jr., Bryan, TX (US); Cesar Benigno Granda, College Station, TX (US)

(73) Assignee: The Texas A&M University System, College Station, TX (US)

( * ) Notice: Subject to any disclaimer, the term of this patent is extended or adjusted under 35 U.S.C. 154(b) by 826 days.

(21) Appl. No.: 11/850,497

(22) Filed: Sep. 5, 2007

(65) Prior Publication Data
US 2008/0121359 A1 May 29, 2008

Related U.S. Application Data

(62) Division of application No. 10/701,409, filed on Oct. 31, 2003, now abandoned.

(60) Provisional application No. 60/423,288, filed on Nov. 1, 2002.

(51) Int. Cl.
*D21C 3/02* (2006.01)
(52) U.S. Cl. .............................. 162/41; 162/57; 162/90
(58) Field of Classification Search ............... 162/90, 162/96, 97, 41, 57
See application file for complete search history.

(56) References Cited

U.S. PATENT DOCUMENTS

| | | | | |
|---|---|---|---|---|
| 614 A * | 2/1838 | Sanderson | ................ | 162/75 |
| 137,484 A * | 4/1873 | Routledge | ................ | 435/278 |
| 1,510,070 A | 9/1924 | Weygang | | |
| 1,724,393 A * | 8/1929 | Walkington et al. | ...... | 106/165.01 |
| 1,857,317 A * | 5/1932 | Millington | ................ | 162/244 |
| 2,193,493 A | 3/1940 | Ritter | ................ | 195/10 |
| 3,586,624 A | 6/1971 | Larson | ................ | 210/3 |
| 3,964,961 A | 6/1976 | Hesch | ................ | 162/96 |
| 4,521,517 A | 6/1985 | Gauthier | ................ | 435/313 |

(Continued)

FOREIGN PATENT DOCUMENTS
WO     9010748     9/1990
(Continued)

OTHER PUBLICATIONS

Gharib et al., In vitro Evaluation of Chemically-treated Poplar Bark, 1975, Journal of animal science, vol. 40 No. 4, p. 734-742.*

(Continued)

*Primary Examiner* — Anthony Calandra
(74) *Attorney, Agent, or Firm* — Timothy S. Westby; Porter Hedges LLP

(57) ABSTRACT

According to one embodiment of the invention, a system for processing biomass includes a water-impermeable bottom liner, a gravel layer supported by the bottom liner, a drain pipe disposed within the gravel layer, a biomass input device operable to deliver biomass over the gravel layer to form a biomass pile, a lime input device operable to deliver lime to the biomass for pretreating the biomass, a distribution pipe elevated above the gravel layer, and a pump operable to circulate water through the biomass pile by delivering water to the distribution pipe and receiving water from the drain pipe after it has traveled through the biomass pile.

According to another embodiment, a method for biomass pretreatment with alkali, conducted at ambient pressure for approximately 4-16 weeks at temperatures ranging from approximately 25° C. to 95° C. Biomass may be lignocellulosic biomass and may be rendered suitable for enzymatic digestion or pulp production.

38 Claims, 28 Drawing Sheets

U.S. PATENT DOCUMENTS

| | | | |
|---|---|---|---|
| 4,668,388 A | 5/1987 | Dibble et al. | 210/150 |
| 5,547,692 A | 8/1996 | Iritani et al. | 426/53 |
| 5,865,898 A | 2/1999 | Holtzapple et al. | 127/37 |

FOREIGN PATENT DOCUMENTS

| | | |
|---|---|---|
| WO | 9015031 | 12/1990 |

OTHER PUBLICATIONS

Smook, Handbook for Pulp and Paper Technologists, 1992, Angus Wilde Publications, 2nd edition, chapter 11.*

Grace editor, Alkaline Pulping, 1989, Joint textbook committee of the Paper Industry, $3^{rd}$ edition, p. 49-55.*

Camber, Rebecca, Sheep poo paper scoops top award, Sep. 2006, Mail Online, whole document.*

Correspondence regarding Application No. 03 786 557.3-2124, Reference No. JL5251; Communication Pursuant to Article 94(3) EPC received from EPO, dated Jul. 28, 2009.

International Search Report with Notification of Transmittal of Search Report, PCT/US03/34942; 8 pages, Mailed Feb. 2, 2004.

European Patent Office 2nd Examination Report dated Jul. 20, 2010 for corresponding EPO Application No. 03786557.3 (2 pgs.).

European Patent Office Communication Under Rule 71(3) dated Oct. 25, 2010 for corresponding EPO Application No. 03786557.3 (3 pgs.).

* cited by examiner

METHODS FOR PRETREATMENT AND PROCESSING OF BIOMASS

PRIORITY CLAIM

This application is a divisional of U.S. application Ser. No. 10/701,409 filed Oct. 31, 2003 and which claims priority under 35 U.S.C. §119(e) to U.S. Provisional Patent Application Ser. No. 60/423,288 filed Nov. 1, 2002.

STATEMENT OF GOVERNMENT INTEREST

Funding from the U.S. Department of Agriculture was used in the development of certain aspects of the present invention. Accordingly, the U.S. government may have certain rights therein.

TECHNICAL FIELD OF THE INVENTION

The present invention relates to processes for biomass treatment, including pretreatment. It also relates to apparatuses for the storage, pretreatment and enzymatic digestion, such as fermentation of such biomass.

BACKGROUND OF THE INVENTION

Treatment of biomass, especially waste biomass, to recover useful substances has been the focus of numerous efforts. Such treatments have used a variety of treatment methods and chemicals, depending upon the desired recovery substance. Treatment with lime ($Ca(OH)_2$ or calcium hydroxide) has been attempted, but usually at temperatures above 60° C. for time frames of only a few weeks to a month.

High-temperature lime treatments have been used to enhance enzymatic digestibility of biomass. One such process uses hot lime only and another uses hot lime+high-pressure oxygen.

Biomass processing is also useful in making pulp. The most common methods for making pulp for paper or cardboard are Kraft and soda pulping. Both of these methods use expensive chemicals and expensive treatment vessels.

Additionally, previous methodologies and treatment systems have often required movement of the biomass several times during the entire treatment process, including pretreatment and recovery. Aspects of the present invention may be used to overcome some of these and other problems associated with previous methodologies.

SUMMARY OF THE INVENTION

One embodiment of the invention relates to a system for processing biomass, including:
  a water-impermeable bottom liner;
  a gravel layer supported by the bottom liner;
  a drain pipe disposed within the gravel layer;
  a biomass input device operable to deliver biomass over the gravel layer to form a biomass pile;
  a lime input device operable to deliver lime to the biomass for pretreating the biomass;
  a distribution pipe elevated above the gravel layer; and
  a pump operable to circulate water through the biomass pile by delivering water to the distribution pipe and receiving water from the drain pipe after it has traveled through the biomass pile.

In more specific embodiments, the biomass may be lignocellulosic biomass, such as bagasse and corn stover. The gravel layer may be approximately three feet thick. The lime input device may be operable to deliver lime to the biomass either during or after the delivering of the biomass over the gravel layer. Lime may be delivered to the biomass in an amount between approximately 10% and 30% of the biomass by weight. Lime pretreatment may occur a temperature between approximately 25° C. and 95° C. at ambient pressure and for a time period greater than approximately four weeks.

The system may also include a heat exchanger coupled to the distribution pipe and operable to control a temperature of the water that is delivered to the distribution pipe. It may also include an air blower and an air distribution pipe operable to deliver air to the biomass pile. A container of lime water slurry may coupled to the air distribution pipe and operable to scrub the air of carbon dioxide before the air is delivered to the biomass pile. A calcium carbonate input device may be added to deliver calcium carbonate to the biomass for pretreating the biomass.

The system may also include an inoculum input device operable to deliver an inoculum to the biomass pile for fermentation of the biomass pile.

Another embodiment of the present invention relates to a system for processing biomass, including:
  a water-impermeable bottom liner;
  a grid-like lattice structure coupled to the bottom liner to form a roof;
  a geomembrane coupled to the grid-like lattice structure;
  a gravel layer supported by the bottom liner;
  a plurality of drain pipes disposed within the gravel layer;
  a conveyor belt coupled to the top liner and operable to deliver biomass over the gravel layer to form a biomass pile;
  a lime input device operable to deliver lime to the biomass for pretreating the biomass;
  a plurality of distribution pipes coupled to the top liner and associated with respective ones of the plurality of drain pipes; and
  a plurality of pumps coupled to respective ones of the plurality of drain pipes and respective ones of the plurality of distribution pipes, the pumps operable to circulate water through the biomass pile by delivering water to the distribution pipes and receiving water from the drain pipes after the water has traveled through the biomass pile.

In more specific embodiments, the biomass may be lignocellulosic biomass such as bagasse and corn stover. The grid-like lattice structure may be formed from a plurality of I-beams in a general shape of a half cylinder. A foam layer may be coupled to an outside of the geomembrane.

The system may also include a sugar extraction device operable to extract sugar from a raw feedstock to produce the biomass. The raw feedstock may be energy cane or sweet sorghum. The sugar extraction device may include a plurality of adjacent extraction tanks, each extraction tank including a screw conveyor operable to deliver solid material from the raw feedstock an a downstream direction and a weir operable to deliver liquid material from the raw feedstock in an upstream direction.

The lime input device may be operable to deliver lime to the biomass either during or after the delivering of the biomass over the gravel layer. The lime pretreatment pile may be maintained at a temperature between approximately 25° C. and 95° C. at ambient pressure and for a time period greater than approximately four weeks. The system may include a heat exchanger coupled to the distribution pipe and operable to control a temperature of the water that is delivered to the distribution pipe. It may also include an air blower and an air distribution pipe operable to deliver air to the biomass pile. A container of lime water slurry may be coupled to the air distribution pipe and operable to scrub the air of carbon dioxide before the air is delivered to the biomass pile. A calcium carbonate input device may be added to deliver calcium carbonate to the biomass for pretreating the biomass.

The system may also include an inoculum input device operable to deliver an inoculum to the biomass pile for fermentation of the biomass pile.

Yet another embodiment of the present invention relates to a system for processing biomass, including:

an end wall;

a water-impermeable bottom liner;

a top liner coupled to the bottom liner, the top liner selectively inflatable by one or more fans coupled to the end wall;

a plurality of water pouches coupled to the top liner, the water pouches selectively inflatable when the top liner is inflated;

a gravel layer supported by bottom liner and separated into a plurality of gravel segments;

a plurality of drain pipes disposed within respective ones of the gravel segments;

a conveyor belt associated with the end wall and operable to deliver biomass over the gravel segments to form a biomass pile;

a lime input device operable to deliver lime to the biomass for pretreating the biomass;

a plurality of distribution pipes coupled to the top liner and associated with respective ones of the plurality of gravel segments; and a plurality of pumps coupled to respective ones of the plurality of drain pipes and respective ones of the plurality of distribution pipes, the pumps operable to circulate water through the biomass pile by delivering water to the distribution pipes and receiving water from the drain pipes after the water has traveled through the biomass pile.

In more specific embodiments, the biomass may be lignocellulosic biomass such as bagasse and corn stover. An opening may formed in the end wall for unloading residue left over from the biomass pile after fermentation. The system may include a sugar extraction device operable to extract sugar from a raw feedstock to produce the biomass. The raw feedstock may be energy cane or sweet sorghum. The sugar extraction device may include a plurality of adjacent extraction tanks, each extraction tank including a screw conveyor operable to deliver solid material from the raw feedstock an a downstream direction and a weir operable to deliver liquid material from the raw feedstock in an upstream direction.

The lime input device may be operable to deliver lime to the biomass either during or after the delivering of the biomass over the gravel layer. The lime pretreatment pile may be maintained at a temperature between approximately 25° C. and 95° C. at ambient pressure and for a time period greater than approximately four weeks. The system may include a heat exchanger coupled to the distribution pipe and operable to control a temperature of the water that is delivered to the distribution pipe. It may also include an air blower and an air distribution pipe operable to deliver air to the biomass pile. A container of lime water slurry may be coupled to the air distribution pipe and operable to scrub the air of carbon dioxide before the air is delivered to the biomass pile. A calcium carbonate input device may be added to deliver calcium carbonate to the biomass for pretreating the biomass.

The system may also include an inoculum input device operable to deliver an inoculum to the biomass pile for fermentation of the biomass pile.

Another embodiment of the invention relates to a system for processing biomass, including:

a plurality of geodesic domes arranged in a generally circular pattern, each geodesic dome comprising:

a water-impermeable bottom liner;
a top liner coupled to the bottom liner;
a gravel layer supported by the bottom liner;
a drain pipe disposed within the gravel layer; and
a distribution pipe elevated above the gravel layer;

a plurality of pumps coupled to respective ones of the plurality of geodesic domes, each pump operable to circulate water through its respective geodesic dome by delivering water to the distribution pipe associated with the respective geodesic dome and receiving water from the drain pipe associated with the respective geodesic dome;

a rotatable conveyor belt surrounded by the geodesic domes and operable to deliver biomass to each geodesic dome; and a lime input device operable to deliver lime to the biomass for pretreating the biomass.

In specific embodiments, the biomass may be lignocellulosic biomass such as bagasse and corn stover. Each top liner may be made of a plurality of hexagonal or pentagonal panels coupled to one another with lips associated with each panel. A foam layer may be coupled to an outside of the top liner. The lime input device may be operable to deliver lime to the biomass either during or after the delivering of the biomass over the gravel layer. A calcium carbonate input device may be added to deliver calcium carbonate to the biomass for pretreating the biomass.

Another embodiment of the present invention relates to a system for processing biomass, including a fermenter structure configured to:

accept and store untreated lignocellulosic biomass;

pretreat the lignocellulosic biomass with lime at a temperature between approximately 25° C. and 95° C. at ambient pressure for a time period greater than four weeks; and treat the lignocellulosic biomass with an inoculant.

One method of the present invention relates to a method of biomass pretreatment by adding an alkali to biomass with lignin content to produce a mixture and incubating the mixture at a temperature between approximately 25° C. and 95° C. at ambient pressure.

In more specific embodiments, the method also includes incubating the mixture for a time period of at least approximately 4 weeks, more specifically between approximately 4 and 16 weeks. The duration of incubation may be selected based on incubation temperature. The biomass may be lignocellulosic biomass such as agricultural waste, bagasse, corn stover and combinations thereof.

The method may also include circulating water through the biomass during incubation and circulating air through the biomass during incubation. The air may be oxygen enriched air. The alkali added may include lime or calcium oxide. When lime is used approximately 0.5 grams of lime may be added per gram of biomass to produce the mixture, or approximately 0.1 to 0.5 grams of lime may be added per gram of biomass to produce the mixture. Alternatively, lime may be added to the biomass in an amount between approximately 10% and 30% of biomass by weight. Calcium carbonate may also be added to the mixture.

The mixture may be incubated at a temperature between approximately 25° C. and 90° C. more specifically between approximately 25° C. and 57° C. The incubation temperature may be based on the partial pressure of water at the selected temperature.

The method may include increasing the enzyme digestibility of the biomass or producing pulp such as pulp suitable for paper or cardboard production.

The method may also include reducing the lignin content of the biomass. Lignin content may be reduced by at least 98%, at least 90%, at least 29%, at least 40%, or at least 67%. Lignin content may be reduced by alkaline oxidation.

The method may also include fermenting the biomass after incubation. The may be accomplished by adding an inoculum to the mixture. After or during fermentation carboxylate salts may be collected from the mixture.

The method may additionally include placing the mixture prior to incubation in a storage facility suitable for incubation and fermentation.

Another method of the present invention relates to a method for producing enzymatically digestible biomass by adding lime to biomass with lignin content to produce a mixture, incubating the mixture at a temperature between approximately 25° C. and 55° C. at ambient pressure for a time period of at least 4 to 16 weeks and circulating water through the mixture during incubation.

In specific embodiments, air may also be circulated through the mixture during incubation. The method may reduce lignin content of the biomass by at least 67%, or at least 32%. Biomass may be fermented after incubation.

Finally, another method of the invention relates to a method for producing pulp by adding lime to biomass with lignin content to produce a mixture, incubating the mixture at a temperature between approximately 45° C. and 55° C. at ambient pressure for a time period of approximately 10 weeks, and circulating water through the mixture during incubation.

In more specific embodiments, the method may include circulating air through the mixture during incubation. The method may reduce lignin content by at least 90% or by at least 40%. The biomass may be used to produce paper or cardboard after fermentation.

For a better understanding of the invention and its advantages, reference may be made to the following description of exemplary embodiments and accompanying drawings in which like features are indicated by like numbers.

DETAILED DESCRIPTION OF THE INVENTION

The present invention includes a method of treating biomass, particularly lignocellulosic biomass, with lime or other alkali to produce useful recovery products. The invention also includes treatment apparatuses that may be used with the lime treatment method or other treatment methods.

The methodology of the present invention includes a process to treat lignocellulosic biomass with lime or other alkali for extended time periods to increase enzymatic digestibility. In addition, lignocellulosic biomass can be treated with lime or alkali and circulated air or oxygen enriched air for extended time periods of time. The methods of the present invention may also be employed to produce pulp, including pulp suitable for making paper or cardboard.

Overall, the processes of the present invention provide very inexpensive ways to process lignocellulosic biomass. Lime is the least expensive alkali and air is free, although circulated or oxygen enriched air may have some associated coats. The treatment conditions in most embodiments are very mild (moderate temperatures, 1 atm pressure) so extremely inexpensive vessels may be employed.

Embodiments of the present invention include pretreatment processes carried out at any of a variety of temperatures ranging from 25° C. (ambient temperature in many regions) to 95° C. Although lime is used in many exemplary embodiments of the present invention, other alkalis including calcium alkalis such as calcium oxide (quick lime) may also be suitable.

Any sort of biomass may be used in the present invention, but lignocellulosic biomass is used in many exemplary embodiments of the invention. The number of weeks the process is carried out may vary from approximately 4-16, depending upon the desired outcome of the process and the temperature at which it operates. Other time periods may also be used to achieve particular results and to accommodate particular conditions, such as starting material, temperature and lime or other alkali concentration. The process conditions and time period of operation to achieve given results for a given starting material will be apparent to one skilled in the art based upon the content of this disclosure and knowledge in the field.

Figure 1:
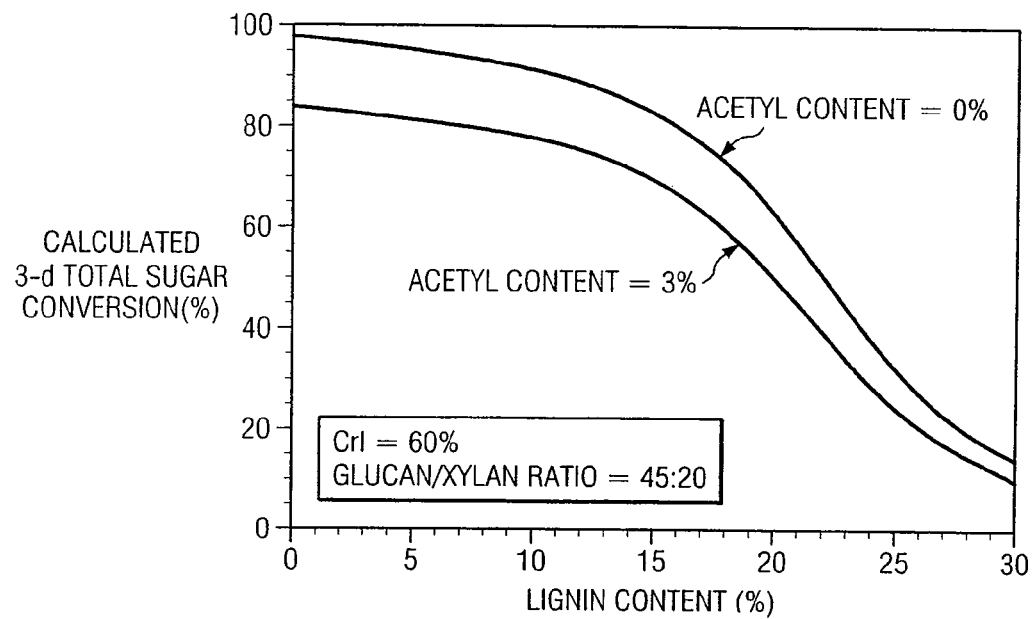
FIG. 1 illustrates the results of a prior art study by Chang and Holtzapple showing the enzymatic digestibility of lignocellulose as a function of lignin content and acetyl content.

FIG. 1 is taken from Vincent S. Chang and Mark T. Holtzapple, Fundamental Factors Affecting Biomass Enzymatic Reactivity, Applied Biochemistry and Biotechnology, Vol. 84-86, pp. 5-36. Native herbaceous lignocellulose typically has about 15-20% lignin and woody lignocellulose has about 25-30% lignin. For both herbaceous and woody biomass, the acetyl content is typically about 3%. FIG. 1 shows that high lignin and high acetyl contents reduce enzymatic digestibility. FIG. 1 indicates that reducing the lignin below the native content substantially increases the enzymatic digestibility; however, when the lignin content reaches 10% or less, the enzymatic reactivity substantially reaches a plateau. Further lignin removal enhances reactivity, but not significantly. FIG. 1 shows that when acetyl groups are removed from the hemicellulose fraction of lignocellulose—for example, by alkaline treatments—the enzymatic reactivity improves as well. FIG. 1 indicates that an ideal lignocellulose treatment process should be capable of removing acetyl groups and also reduce the lignin content to at least about 10%.

Although lignin reduction below 10% benefits enzymatic reactivity slightly, the additional cost imposed by further reduction may not be justified. In contrast, if the goal is to make pulp for paper or cardboard, then it is desirable to remove as much lignin as possible. Ideally for paper, the lignin content is zero, although this usually requires expensive bleaching as a final step.

The apparati of the present invention include a combined storage and pretreatment systems. Other embodiments include a system also suitable for fermentation. The systems include a lined fermentor into which untreated biomass may be placed. The untreated biomass may then be pretreated with, for example, lime. Water may be moved through the biomass pile by an assembly of pumps and pipes that collect water from the bottom of the pile and distribute it to the top of the pile. After pretreatment is complete, the pile may be subject to further treatment, such as fermentation. Although the primary pretreatment agent is referred to as lime in the description of apparati, one skilled in the art will understand that other or additional alkali may be used in specific embodiments in a manner similar to lime.

Figure 2:
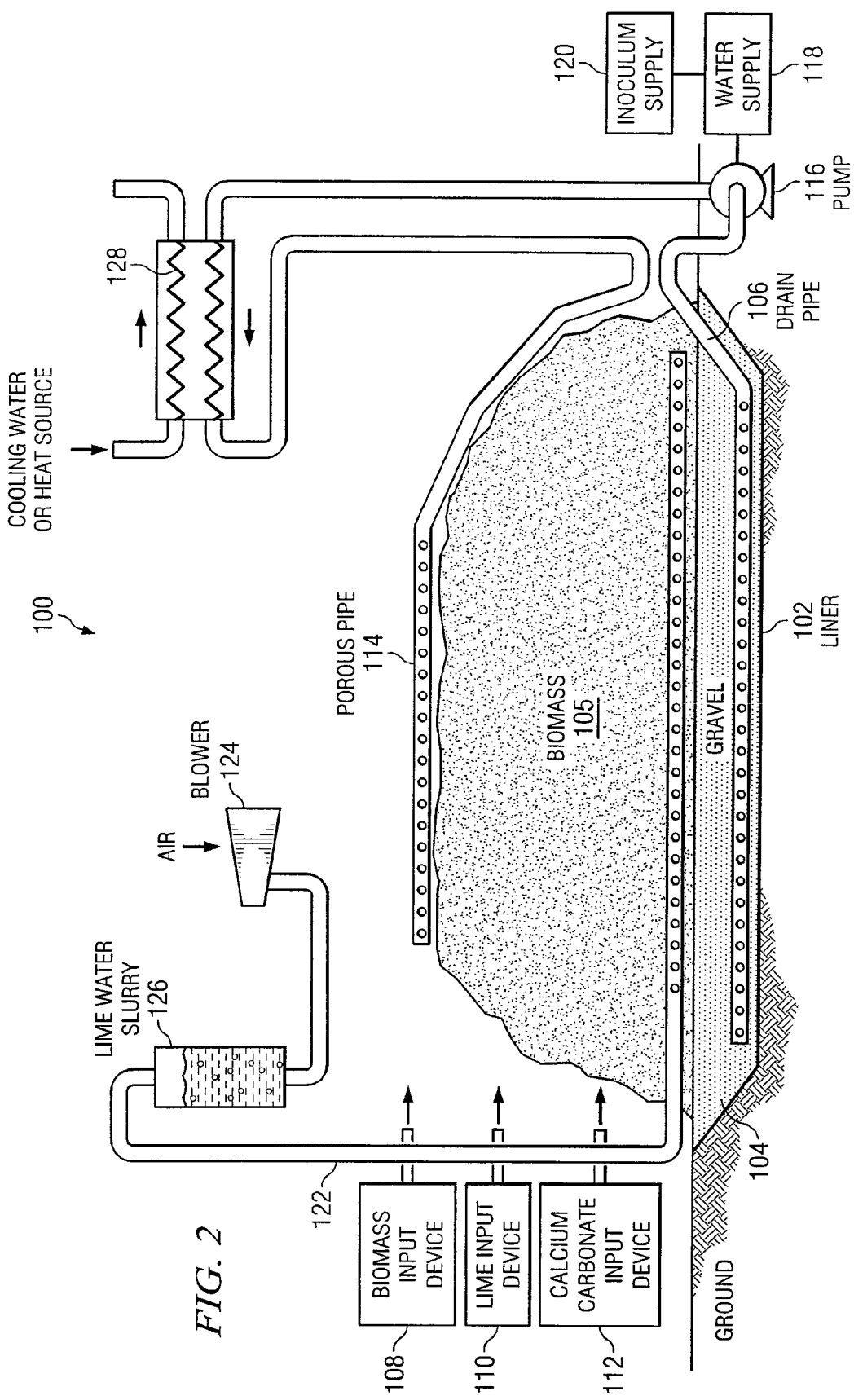
FIG. 2 is a schematic of a system for processing biomass according to an embodiment of the present invention.

FIG. 2 is a schematic of a system 100 for processing biomass according to an embodiment of the present invention. In the illustrated embodiment, system 100 includes a water-impermeable bottom liner 102, a gravel layer 104, a drain pipe 106, a biomass input device 108, a lime input device 110, a calcium carbonate input device 112, a distribution pipe 114, a pump 116, a water supply 118, an inoculum supply 120, an air distribution pipe 122, an air blower 124, a lime water slurry container 126, and a heat exchanger 128. The present invention contemplates more, less, or different components for system 100 than those shown in FIG. 2.

An important advantage of system 100, and other example systems described below in conjunction with FIGS. 3-17, is that a single facility may be utilized to accept and store untreated biomass, pretreat the biomass, and ferment the biomass, which reduces biomass handling by allowing three operations to be accomplished in a single storage facility. Solids transport may be accomplished using well established techniques so there is little risk associated with handling biomass. Also, fermentation may occur up to almost a full year, the product concentration may be very high, thus reducing dewatering costs. Previous biomass processing systems had to utilize high temperatures and high pressures, which increased the cost of the storage facilities and decreased the quality of the product obtained.

Liner 102, which may be formed from any suitable water-impermeable material, functions to support gravel layer 104 and prevent any water or other material from entering the ground. Although liner 102 may be placed upon any suitable support, it is preferable that liner 102 lie in a suitable pit or bermed wall in the ground. Liner 102 may have any suitable shape and the depth of liner 102 should be suitable to handle a desired amount of gravel for gravel layer 104. An example depth for gravel layer 104 is approximately three feet; however, other suitable depths may also be utilized for gravel layer 104. Gravel layer 104 is comprised of any suitable loose or unconsolidated deposit of rounded pebbles, cobbles, boulders, or other suitable stone-like material that functions to allow water to flow relatively freely therethrough.

On top of gravel layer 104 is a biomass pile 105 that is delivered over gravel layer 104 via biomass input device 108. Biomass input device 108 represents any suitable device for creating biomass pile 105, such as a suitable conveyer system, front end loader, or other suitable delivery system. As described above, the biomass forming biomass pile 105, in one embodiment, is lignocellulosic biomass, such as bagasse, corn stover, or other suitable biomass.

Lime input device 110 and calcium carbonate input device 112 are any suitable devices operable to deliver lime and calcium carbonate, respectively, to the biomass as biomass pile 105 is being formed. In other embodiments, the lime and/or calcium carbonate is delivered after biomass pile 105 is formed. As described above, lime is utilized to pretreat the biomass and, in some embodiments, calcium carbonate 112 may also be used to pretreat the biomass. Although the amount of lime added to biomass pile 105 may vary depending on the type of biomass, in one embodiment, an amount of lime delivered to biomass pile 105 is between approximately 10% and 30% of the biomass by weight.

Water from water supply 118 is circulated through biomass pile 105 by pump 116 by delivering the water through distribution pipe 114, which may be any suitable perforated conduit and is elevated above biomass pile 105, and recovering the water through drainpipe 106 after it has traveled through biomass pile 105 and gravel layer 104. Circulation may either be continuous with a relatively low flow rate or may be intermittent with a relatively high flow rate. With a continuous circulation and low flow rate, channeling may occur which is undesirable because some portions of biomass pile 105 may not be wetted. Uneven wetting of biomass pile 105 may cause the following problems: incomplete pretreatment of biomass pile 105, poor temperature control, and spontaneous combustion of dried portions of biomass pile 105. An intermittent circulation and high flow rate periodically floods biomass pile 105, thus ensuring all or most portions are wetted, thereby overcoming the potential problems of continuous circulation with low flow rate.

The temperature of the water circulated through biomass pile 105 may be regulated by heat exchanger 128. Heat exchanger 128 may be any suitable device used to control the temperature of the water circulated through biomass pile 105. For example, heat exchanger 128 may be a shell-and-tube type heat exchanger.

While biomass pile 105 is being pretreated, air may be blown upward through biomass pile 105 to enhance lignin removal by alkaline oxidation. This may be facilitated by air blower 124 forcing air through air distribution pipe 122, which may be any suitable perforated conduit disposed proximate gravel layer 104. Because air contains carbon dioxide, it may react with lime to form calcium carbonate, an unproductive reaction. To prevent this from occurring in biomass pile 105, the air may be scrubbed of carbon dioxide by passing it through lime water slurry in container 126, which may be a suitable packed column or tank. Oxygen enriched or may also be used.

As described above, biomass pile 105 may be subject to a fermentation process while disposed over gravel layer 104. To facilitate the fermentation after pretreatment is complete, water is circulated through biomass pile 105 that contains an inoculum of acid-forming microorganisms obtained from inoculum supply 120. The acid-forming microorganism start to degrade biomass pile 105 forming carboxylic acids that react with calcium carbonate to form calcium carboxylate salts. Water may then be circulated through biomass pile 105 to remove the carboxylate salts.

The storage, pretreatment, and fermentation of biomass may also be accomplished using other suitable storage facilities or systems. Various embodiments of these systems are described below in conjunction with FIGS. 3-17.

Figure 3:
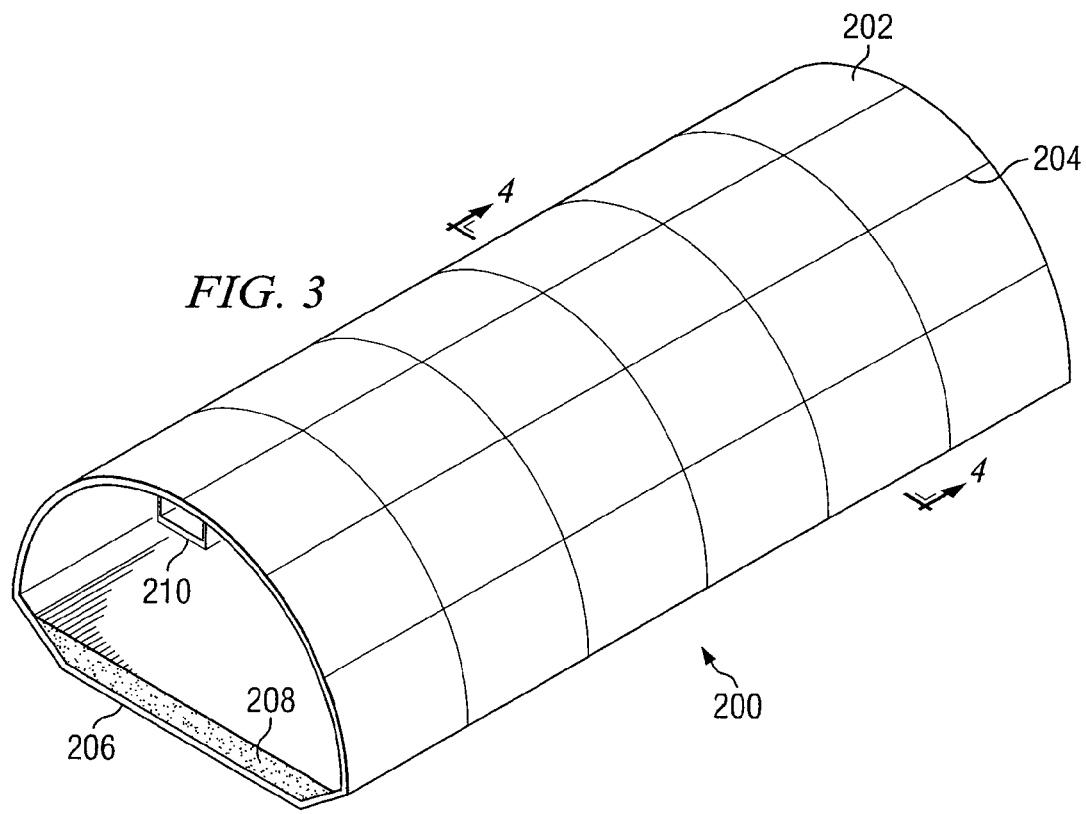
FIG. 3 illustrates a fermenter according to an embodiment of the present invention.
Figure 4:
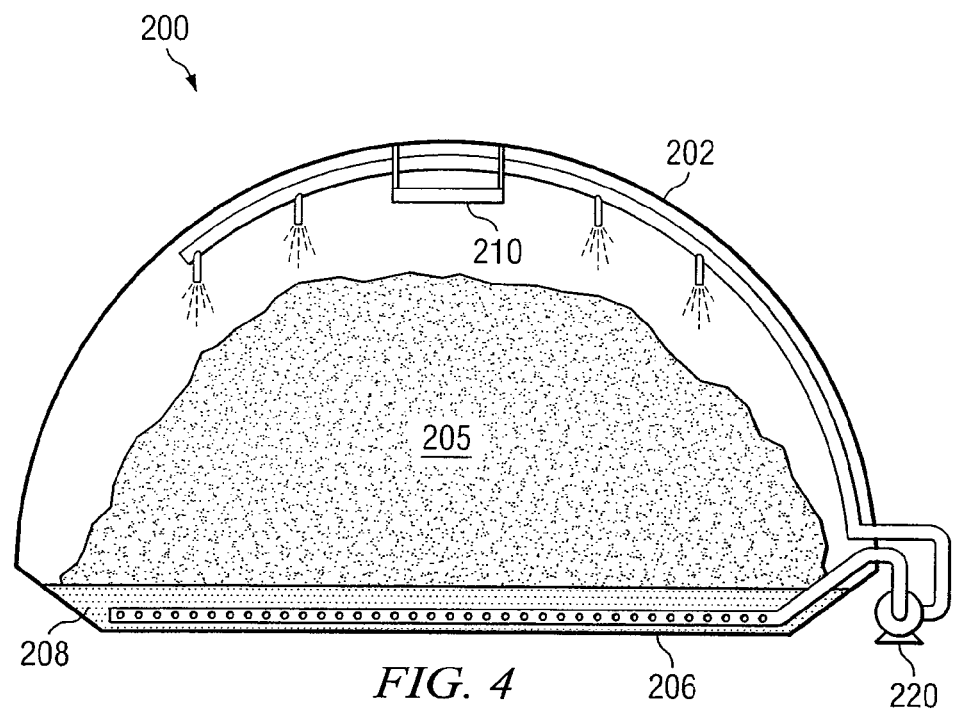
FIG. 4 is a cross-sectional view of the fermenter of FIG. 3 illustrating a biomass pile therein according to an embodiment of the present invention.

FIGS. 3 and 4 are perspective and cross-sectional views, respectively, of a system 200 for storing, pretreating, and fermenting biomass in accordance with another embodiment of the invention. System 200 is similar to system 100 in FIG. 2; however, system 200 includes a geomembrane 202 coupled to a grid-like lattice structure 204 to form a roof for the facility. In the illustrated embodiment, grid-like lattice structure 204 is formed from any suitable structural beams, such as I-beams, and has any suitable shape, such as a half cylinder shape, an arch, or other shapes suitable to form an enclosure between geomembrane 202 and a bottom liner 206 that supports a gravel layer 208.

Grid-like lattice structure 204 includes a conveyer belt 210 coupled thereto and running along the length of grid-like structure 204 to deliver biomass within the enclosure and over gravel layer 208. Any suitable conveyer system is contemplated by the present invention for conveyer belt 210. In addition, conveyer belt 210 may be coupled to grid-like lattice structure 204 in any suitable manner.

Figure 5:
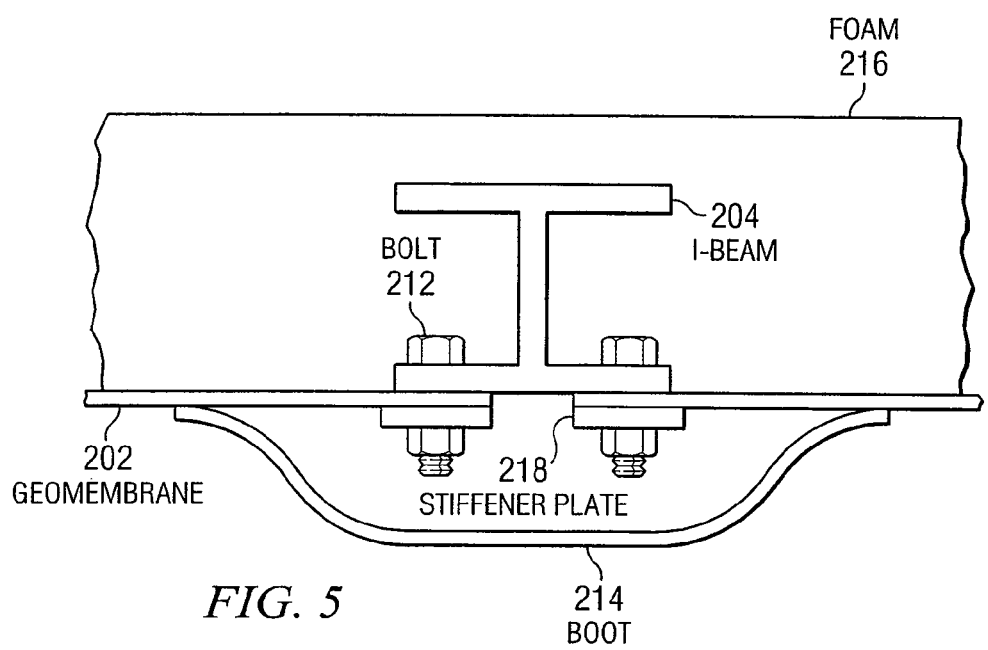
FIG. 5 illustrates a detail of how a geomembrane may be coupled to the fermenter of FIG. 3 according to an embodiment of the present invention.

Geomembrane 202, which may be formed from any suitable material, may be coupled to grid-like lattice structure 204 in any suitable manner; however, one embodiment of coupling geomembrane 202 to grid-like lattice structure 204 is illustrated below in conjunction with FIG. 5. Referring to FIG. 5, one or more bolts 212 are utilized to couple geomembrane 202 to grid-like lattice structure 204. To prevent the corrosion of bolts 212 or grid-like lattice structure 204, a boot 214 formed from the same or similar material as geomembrane 202 is utilized to cover bolts 212. Other suitable fasteners other than bolts may also be utilized to couple geomembrane 202 to lattice structure 204. A pair of stiffener plates 218 may provide stiffness to geomembrane 202, which is disposed between stiffener plates 218 and lattice structure 204 and coupled therebetween by bolts 212.

Also illustrated in FIG. 5 is a foam layer 216 coupled to an outside surface of geomembrane 202. Any suitable foam material may be utilized for foam layer 216 and it may be coupled to an outside surface of geomembrane 202 using any suitable method, such as a spray-in-place method. Foam layer 216 functions to make the exterior somewhat rigid to prevent geomembrane 202 from flexing in the wind, which may lead to possible fatigue failure. Although not illustrated, foam layer 216 may be painted or otherwise coated with a suitable coating to resist UV damage.

Figure 6:
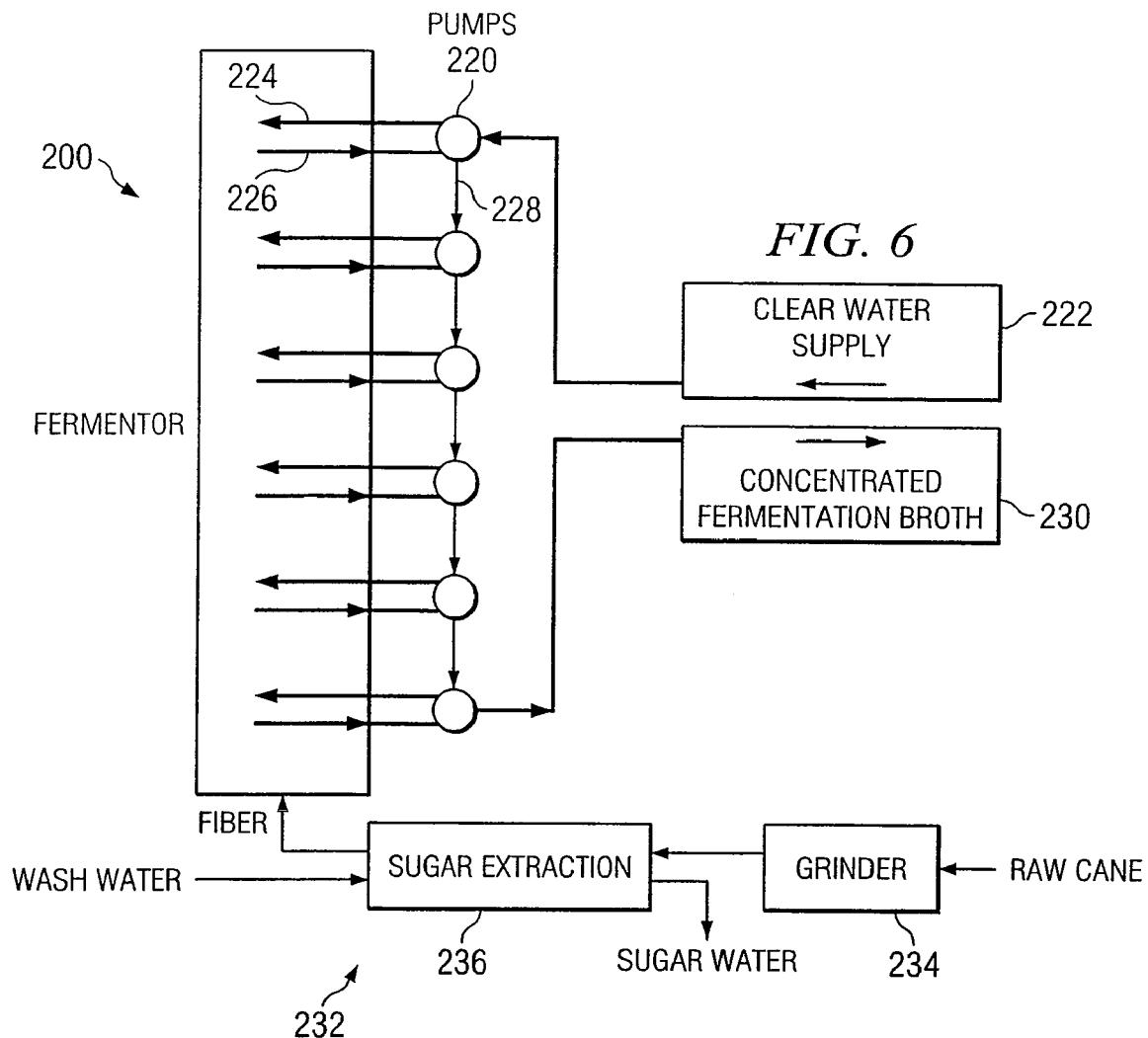
FIG. 6 is a schematic of a fermenter layout according to an embodiment of the present invention.

FIG. 6 illustrates a plan view of system 200 according to an embodiment of the invention. A plurality of pumps 220 are suitably located adjacent system 200 to pump clear water from clear water supply 222 through a suitable conduit system to distribution pipes 224 coupled to geomembrane 202 and that are operable to direct the water towards biomass pile 205. A plurality of drain pipes 226 associated with respective distribution pipes 224 may be utilized to collect the water after it has traveled through biomass pile 205 and be recirculated by pumps 220. A small side stream, as denoted by reference number 228, may be pumped from each pump 220 to its adjacent pump 220.

In one embodiment, clear water from clear water supply 222 is introduced to one end of system 200, thereby establishing a concentration gradient along biomass pile 205. A portion of biomass pile 205 with the most dilute carboxylate salts reacts more rapidly because there is less inhibition. Eventually, the entire biomass pile 205 is reacted. By adjusting the rate water is pumped to adjacent pumps 220, the reaction rate may be regulated so that the reaction is completed a few weeks prior to harvesting the next season's crop. Solid residues that remain in the enclosure (for example, lignin, unreacted carbohydrates, may be removed using front-end loaders, dump trucks, or other suitable devices). After fermentation of biomass pile 205, the resulting products, as represented by concentrated fermentation broth 230 in FIG. 6, may be removed using pumps 220.

Also illustrated in FIG. 6 is a system 232 for delivering biomass to conveyer belt 210 according to one embodiment of the invention. In the illustrated embodiment, system 232 includes a grinder 234 and a sugar extraction device 236. Grinder 234 receives a suitable feedstock, such as raw energy cane, and processes it before delivering it to sugar extraction device 236. Feedstock other than raw energy may be also utilized, such as high-yield sweet sorghum. To make best use of the sugars in the feedstock, the sugars may be extracted and sold for food or as feedstock for pure-culture fermentations (for example, ethanol, and citric acid). Grinder 234 may be any suitable grinder, such as a hammer mill, operable to grind raw feedstock. Sugars are then extracted using sugar extraction device 236.

Sugar extraction device 236 may be a conventional sugar mill that uses high pressure rollers to squeeze sugars out of energy cane. Sugar cane varieties with high sugar concentration may be employed to maximize the amount of sugar produced from each roller. Wash water may be circulated through sugar extraction device 236 in order to extract sugar water therefrom. The feedstock coming out of sugar extraction device 236 is the biomass that is delivered to system 200 using conveyer belt 210 or other suitable delivery system.

To reduce the cost of extracting sugars from raw feedstock, a low-cost method is desirable. An example low-cost method is illustrated below in conjunction with FIG. 7, which shows a multi-stage countercurrent sugar extractor 300 according to one embodiment of the invention. The larger arrows 302 illustrate solids flow and the smaller arrows 304 illustrate liquid flow. Extractor 300 includes a plurality of adjacent extraction tanks 306, wherein each extraction tank 306 includes a screw conveyer 308, as illustrated in FIG. 8, and a weir 310, as illustrated in FIG. 9.

Figure 7:
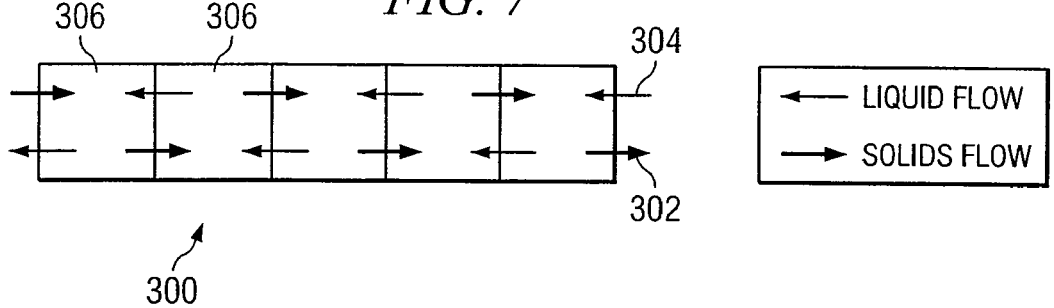
FIG. 7 is a schematic of a multi-stage countercurrent extractor according to an embodiment of the present invention.
Figure 8:
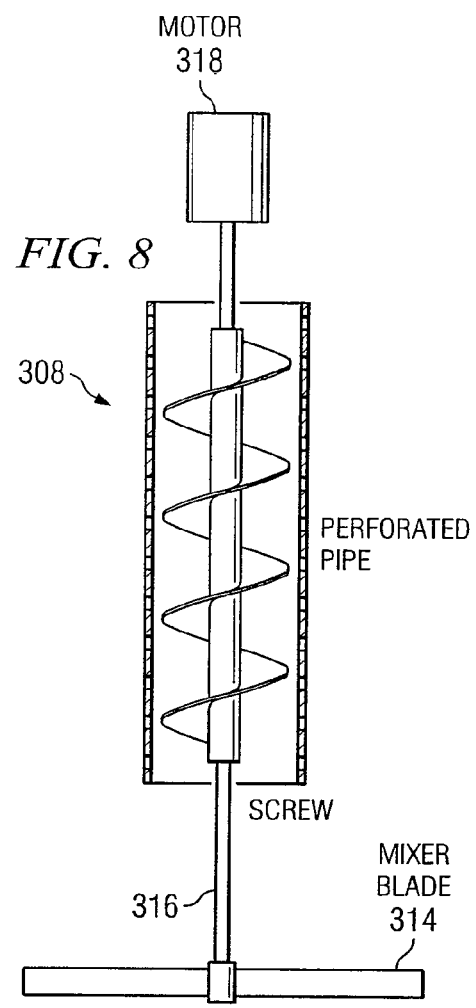
FIG. 8 is a schematic of a screw press with mixing blade according to an embodiment of the present invention.

Referring to FIGS. 7 and 8, a feedstock slurry with a high water content is disposed within extraction tank 306. Screw conveyer 308, which may be any suitable conical screw conveyer, transports the slurry upward in the expanding cone of conveyer 308. This allows less room, which forces water out of the slurry causing it to exit through the perforated pipe 312 of conveyer 308 and back down towards the interior of extraction tank 306.

To achieve mixing in the high water slurry, a mixer blade 314 may be employed on the end of shaft 316 of conveyer 308. This allows a single motor 318 to drive both mixer blade 314 and the conical portion of screw conveyer 308, which saves capital costs. Weir 310 is protected from the agitation resulting from mixer blade 314, thereby allowing the biomass to settle so liquid selectively flows over weir 310 to the preceding extraction tank 306. In one embodiment, a screen (not shown) is employed on weir 310 to filter out solids. To prevent possible degradation of sugars in extraction tank 306, lime may be added to maintain a sufficiently high pH so that microorganisms cannot grow. To take advantage of the mixing, all the fermentation lime and calcium carbonate may be added in the last extraction tank 306 prior to discharging the solid biomass.

Figure 9:
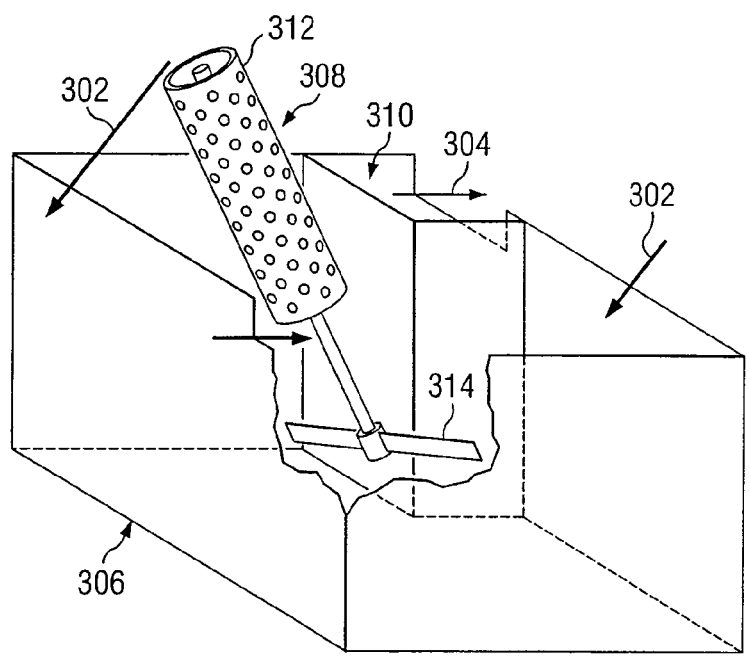
FIG. 9 is a schematic of a screw mounted at an angle according to an embodiment of the present invention.

Referring to FIG. 9, the water flow is represented by arrow 304 and the solids flow is represented by 302. The adjacent extraction tanks 306 are not illustrated in FIG. 9 for clarity of description purposes. Conveyer 308 is tilted at a suitable angle in order to facilitate the delivering of the solids to the downstream extraction tanks 306.

Figure 10:
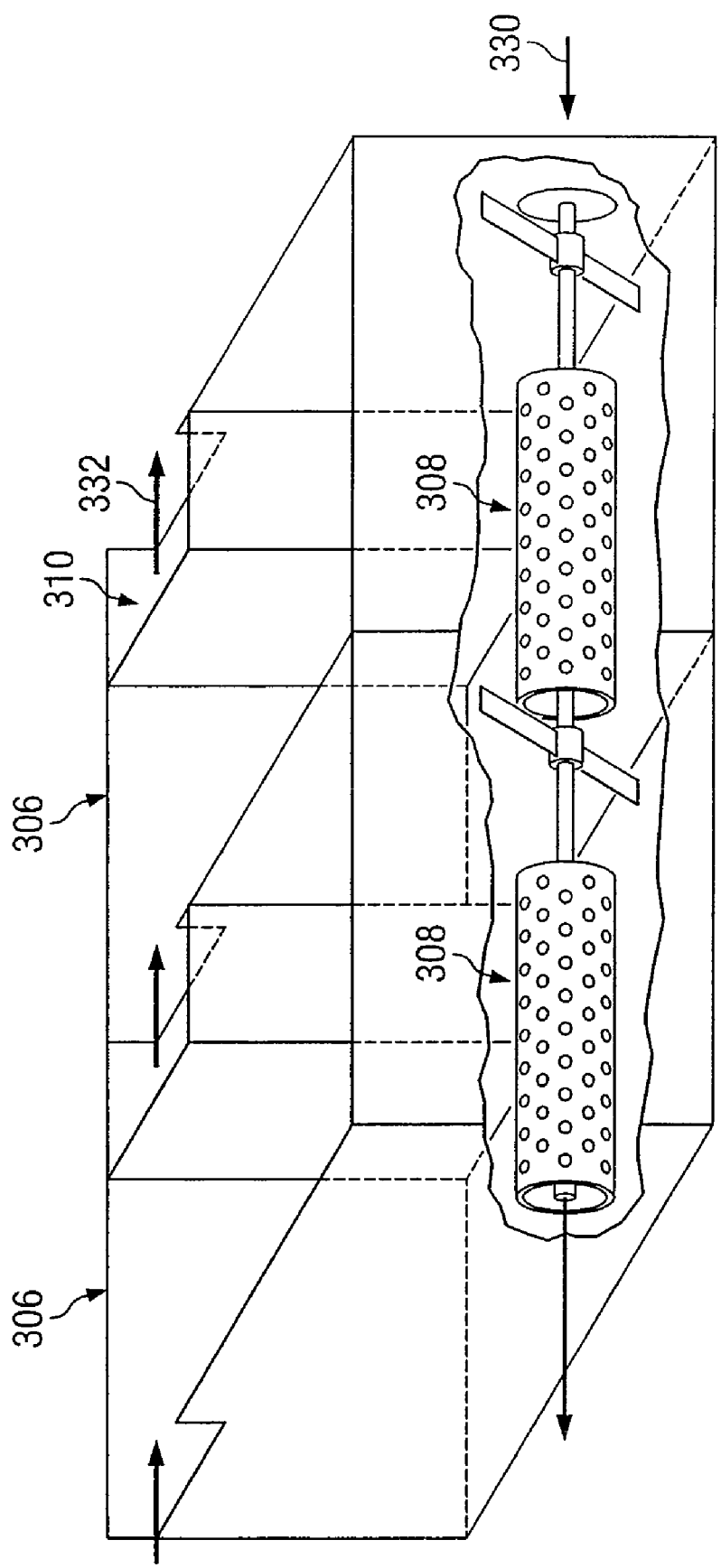
FIG. 10 is a schematic of tanks for use with a horizontal screw according to an embodiment of the present invention.

FIG. 10 is a schematic of extraction tanks 306 according to another embodiment of the present invention. FIG. 10 illustrates how the screw conveyers 308 may be mounted horizontally in extraction tanks 306 to achieve the countercurrent flow of solids and liquids. As illustrated in FIG. 10, the large arrows 330 illustrate solids flow while the small arrows 332 illustrate the liquid flow over weirs 310. Multiple screws conveyors 308 may be located in a single extraction tank 306, thus giving a large perforated surface area through which the water may easily flow. One advantage of the horizontal configuration for conveyers 308 in FIG. 10 is that a single motor (not explicitly shown) may service multiple extraction tanks 306, thus reducing capital costs.

Figure 11:
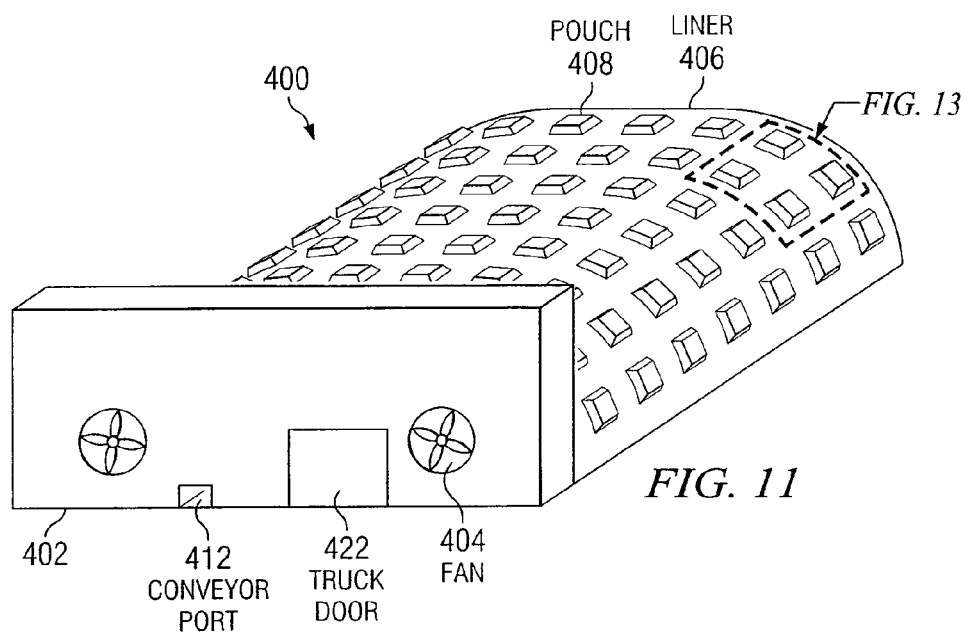
FIG. 11 illustrates a fermenter according to another embodiment of the present invention.
Figure 12A:
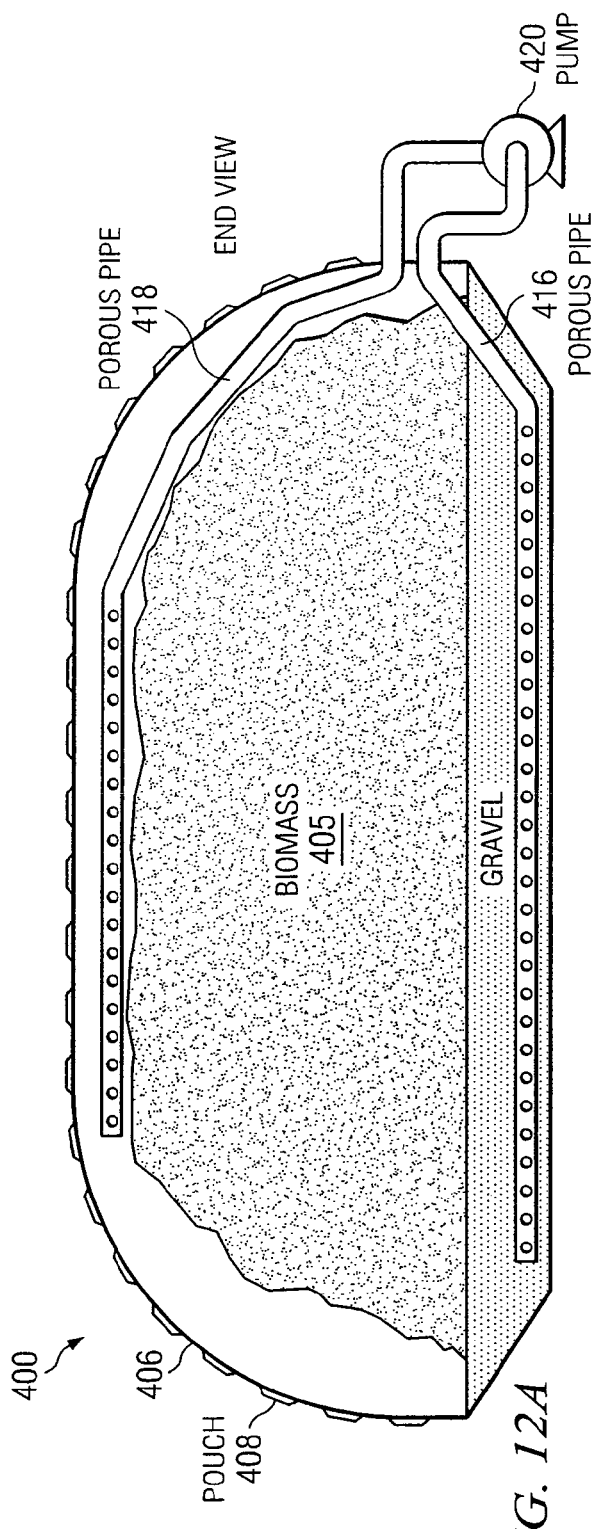
FIGS. 12A and 12B are various cross-sectional views of the fermenter of FIG. 11 illustrating a biomass pile therein according to an embodiment of the present invention.
Figure 12B:
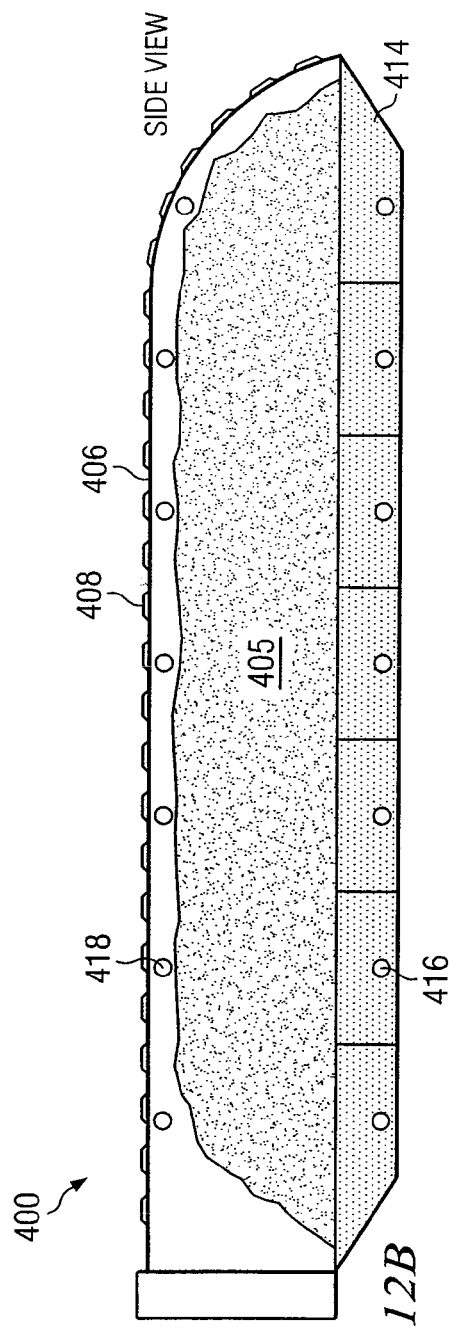

FIG. 11 is a perspective view and FIGS. 12A and 12B are various cross-sectional views of a system 400 for storing, pre-treating, and fermenting biomass in accordance with another embodiment of the invention. System 400 is similar to system 200 described above; however, system 400 includes an end wall 402, which may be any suitable rigid structure, having one or more fans 404 that are operable to selectively inflate a top liner 406 having a plurality of selectively inflatable pouches 408 coupled thereto. In this manner, top liner 406 may be in a deflated state when not in use and, when desired to store, pre-treat and ferment biomass therein, top liner 406 may be inflated by fans 404 to form an enclosure for the biomass. Top liner 406 may be formed from any suitable inflatable material, such as plastic, which functions to exclude rain water and to maintain anaerobic conditions within the enclosure. To prevent top liner 406 from deflecting in the wind, pouches 408 are filled with water or other suitable liquid using any suitable conduit system. Details of pouches 408 are illustrated below in conjunction with FIG. 13.

Figure 13:
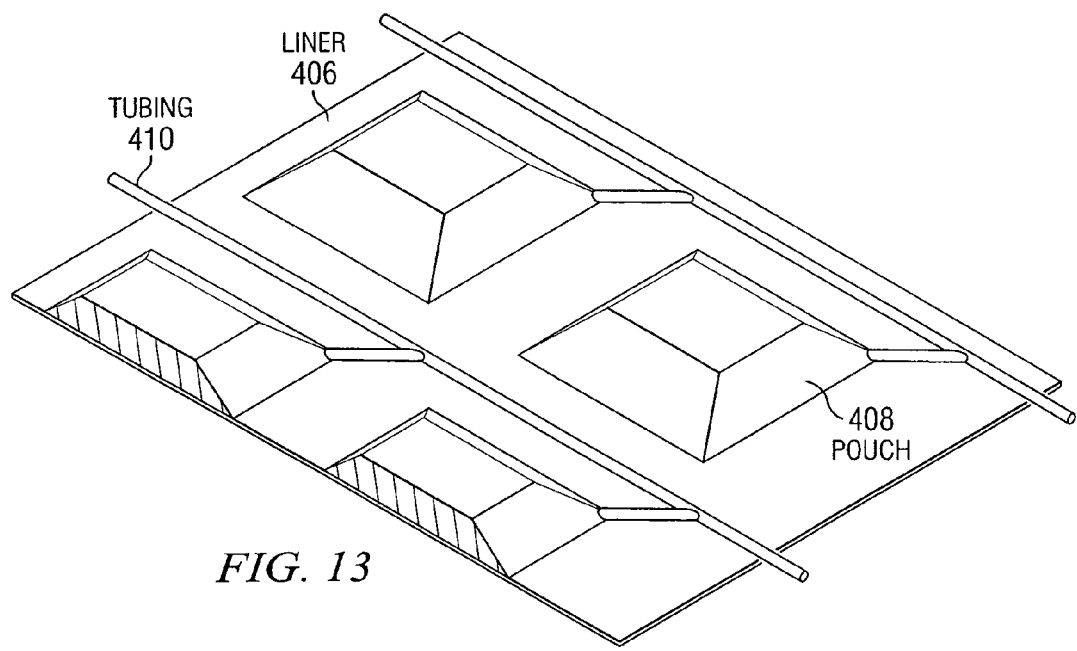
FIG. 13 is a perspective view of water-filed pouches for use in the fermenter of FIG. 11 according to an embodiment of the present invention.

Referring to FIG. 13, a portion of top liner 406 is illustrated with some of pouches 408. Suitable conduits 410 are illustrated as delivering water or other liquid to and from pouches 408 in order to inflate or deflate pouches 408 as desired. Pouches 408 may be formed from any suitable inflatable material and may be formed with any suitable configuration and arrangement.

Referring back to FIGS. 11, 12A and 12B, end wall 402 also includes a conveyor port 412 that functions to accept a suitable conveyor system for delivering the biomass to the inside of the structure. Inside the structure is a suitable gravel layer 414 that is, in the illustrated embodiment, divided into a plurality of segments. Each of these segments includes a drain pipe 416 and a distribution pipe 418 that are coupled to a suitable pump 420 for the purpose of circulating water through biomass pile 405. Also illustrated in FIG. 11 is a truck door 422 suitable for allowing end loaders or other suitable equipment to remove the residue left over after the fermentation of biomass pile 405.

Figure 14:
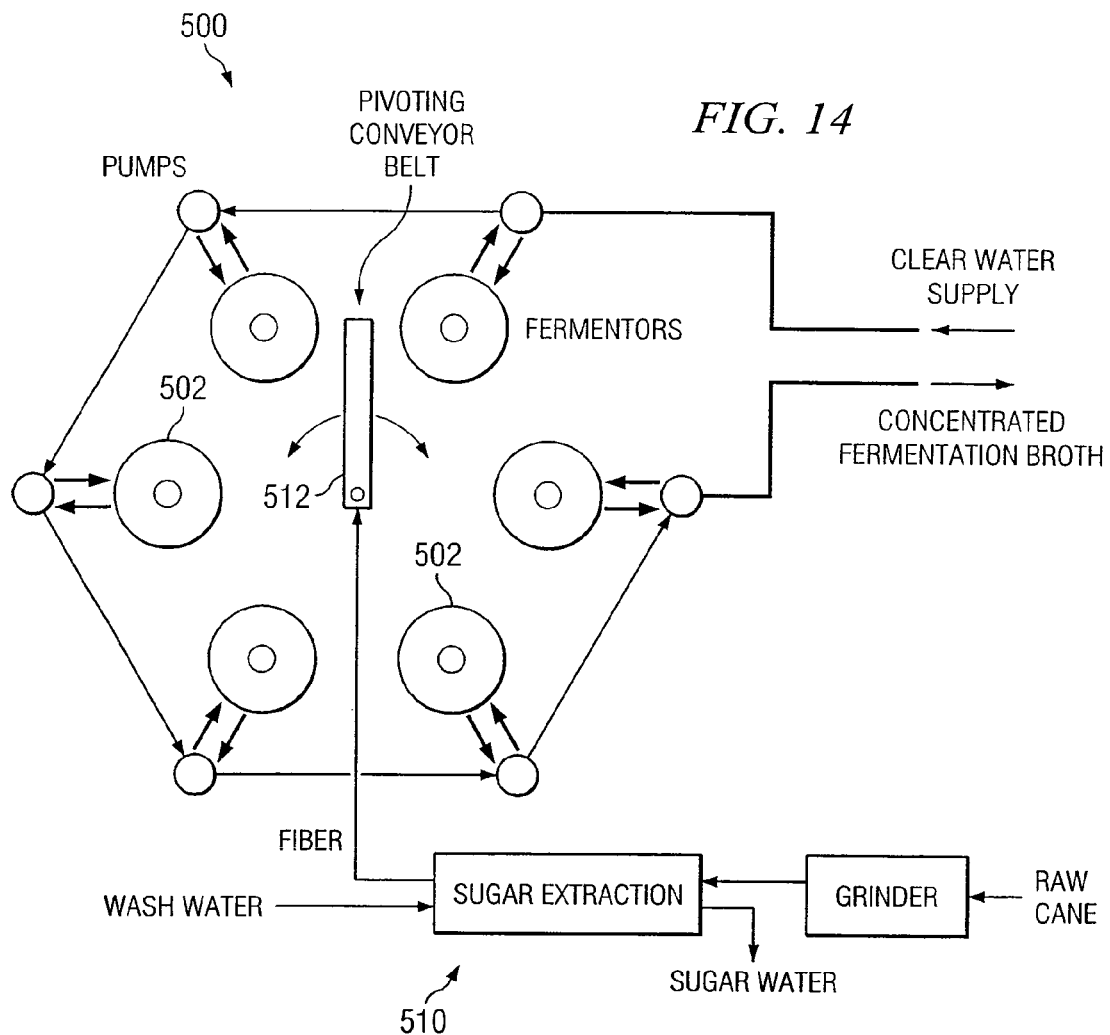
FIG. 14 is a schematic of a fermenter layout for another embodiment of the present invention.
Figure 15A:
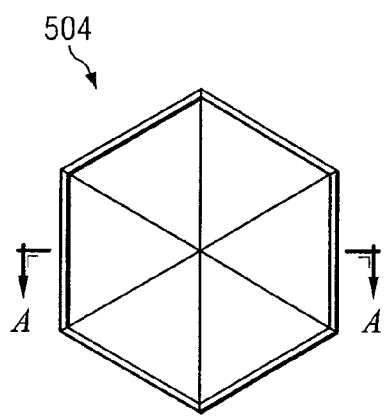
FIGS. 15A and 15B are top and cross-sectional views, respectively, of a hexagonal panel in a geodesic dome fermenter according to another embodiment of the present invention.
Figure 15B:
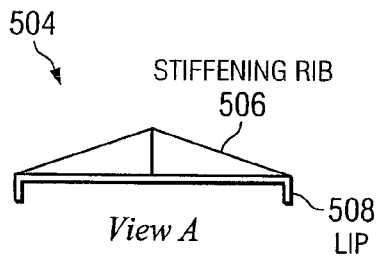

FIG. 14 is a schematic of a system 500 for processing biomass according to one embodiment of the invention. In the illustrated embodiment, system 500 includes a plurality of geodesic domes 502 arranged in a generally circular pattern, wherein each geodesic dome 502 includes similar system components to those illustrated above in conjunction with systems 100, 200, and 400. As illustrated in FIGS. 15A and 15B, the roof of each geodesic dome 502 is constructed from a plurality of panels 504 having stiffening ribs 506 and a lip 508 for coupling panels 504 to one another. Panels 504 may be any suitable shape, such as hexagonal or pentagonal, and may be formed from any suitable material. Panels 504 may also be coupled to one another along lips 508 using any suitable method, such as plastic welding.

Figure 16:
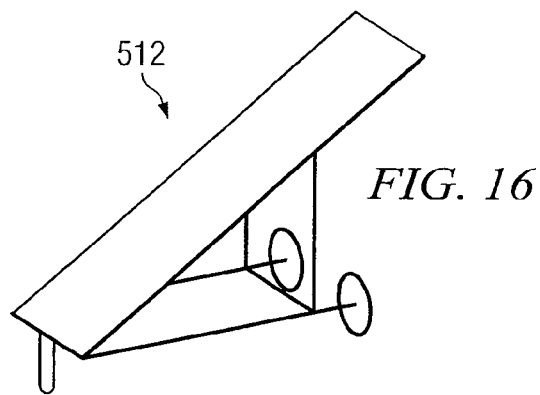
FIG. 16 is a schematic of a pivoting conveyor belt for use in an embodiment of the present invention.

Referring back to FIG. 14, a biomass delivery system 510, with similar components to those described above in conjunction with FIG. 6, delivers biomass to a pivoting conveyor belt 512, as shown below in conjunction with FIG. 16. Any suitable rotatable conveyor belt system may be utilized for conveyor belt 512. Conveyor belt 512 is surrounded by geodesic domes 502 and functions to deliver biomass to each of the geodesic domes 502. Each geodesic dome 502 may have a hole near the top into which the biomass enters. Once the biomass pile is built, then the hole may be closed using any suitable method. Foam (not shown) may also be coupled to an exterior of geodesic domes 502 to provide stiffness, plug holes, and protect the tops of the geodesic domes from the environment. One advantage of the embodiment illustrated in FIG. 14 is that multiple individual facilities give greater flexibility when scheduling filling, pre-treatment, fermentation, and emptying of biomass.

Figure 17:
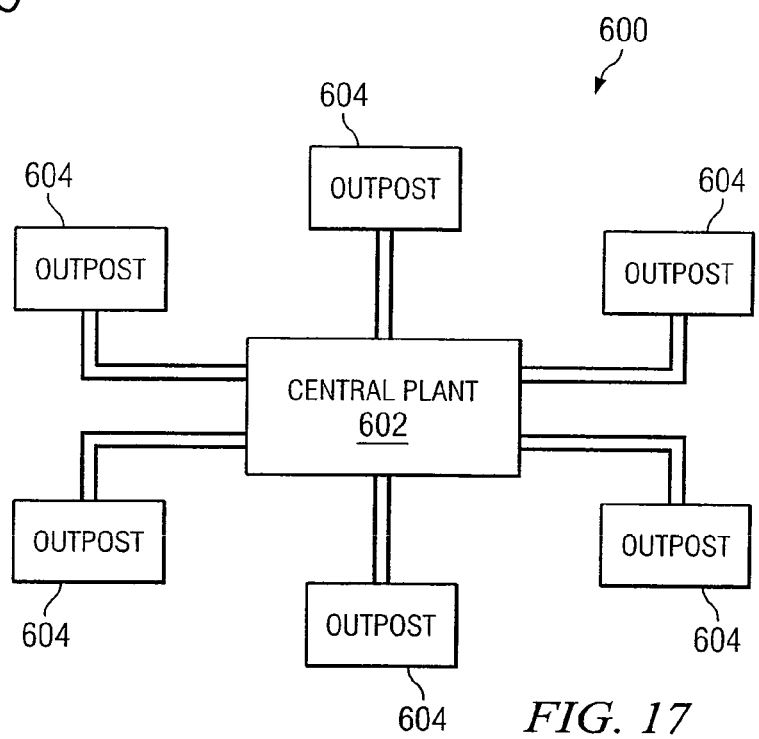
FIG. 17 is a schematic of a large biomass processing plant with fermenters located in the outposts according to an embodiment of the present invention.

FIG. 17 illustrates a system 600 processing biomass according to another embodiment of the present invention. FIG. 17 illustrates that the shipping distance of raw biomass to a central plant 602 may be reduced by connecting a plurality of outposts 604 to central plant 602 via suitable conduits, such as pipelines. Each outpost 604 would include the components illustrated in any of the systems described above. During the harvest season, the pipelines would shift sugar water to central plant 602 for purification. Once the biomass pile has been built and the pre-treatment is complete, then the pipeline may be used to ship fermenter broth solutions to central plant 602 for concentration and conversion to useful products, such as ketones, alcohols, and carboxylic acids.

The following examples are included to demonstrate specific embodiments of the invention. Those of skill in the art should, in light of the present disclosure, appreciate that many changes may be made in the specific embodiments which are disclosed and still obtain a like or similar result without departing from the spirit and scope of the invention.

EXAMPLES

Example 1

General Pretreatment Conditions

Specific embodiments of the present invention include lignocellulosic biomass treatment with lime only or lime with circulated air, including oxygen enriched air. Such embodiments may be used to treat, for instance corn stover and bagasse. The general conditions of these embodiments are as follows:

Pressure: 1 atm or ambient pressure to avoid the need for pressure vessels.

Temperature: Temperatures ranging from 25 to 57° C. As expected, lignin removal is more rapid at higher temperatures. In principle, the reaction could be operated as high as 100° C. and the pressure would remain 1 atm. However, at 100° C., the partial pressure of water would be 1 atm and the partial pressure of air would be 0 atm. In this case, the benefits of oxidizing the lignin could not be realized. Therefore, it is advisable to reduce the temperature to reduce the water partial pressure. The following table provides guidance in temperature selection:

| Temperature (° C.) | Water Partial Pressure (atm) |
|---|---|
| 50 | 0.121 |
| 60 | 0.197 |
| 70 | 0.308 |
| 80 | 0.468 |
| 90 | 0.692 |
| 95 | 0.834 |

In an exemplary embodiment, 90° C. is the upper temperature limit because above this temperature the partial pressure of air is too low for effective lignin degradation.

Lime Loading: Lime is consumed due to reactions within the biomass and it also reacts with carbon dioxide in the purged air. However, in most embodiments, a lime loading of 0.5 g $Ca(OH)_2$/g biomass is sufficient to obtained desired pretreatment outcomes. Lime loading can be lowered to about 0.1 to 0.35 g $Ca(OH)_2$/g biomass, depending on the time and temperature. Lime only treatment (without circulated air) is not optimal for making pulp because lignin removal is not sufficient, however it may be more than sufficient for preparing biomass for later enzymatic digestion. The advantage of lime only pretreatment is that lime consumption is generally less than in the lime with circulated air pretreatment embodiments. Also, the expense of air addition is eliminated.

Time: To enhance biomass digestibility, the following times are general guidelines:

| Temperature (° C.) | Time (weeks) |
|---|---|
| 25 | 16 |
| 35 | 16 |
| 45 | 8 |
| 55 | 4 |

These time/temperatures are guidelines, not firm requirements and may be varied depending upon other reaction conditions, such as pressure and lime loading.

To produce pulp for paper or cardboard, more lignin is preferably removed than when enhancement of enzymatic digestibility is the desired outcome of the process. For production of pulp, the following times are general guidelines:

| Temperature (° C.) | Time (weeks) |
|---|---|
| 45 | >10 |
| 55 | >10 |

These time/temperatures are guidelines, not firm requirements and may be varied depending upon other reaction conditions, such as pressure and lime loading.

Air: Access to circulated air and hence oxygen in a biomass pile is limited. However, the presence of circulated air or oxygen enriched air (including pure oxygen) significantly enhances the removal of lignin. Therefore, in some embodiments of the present invention, the biomass pile is supplied with circulated air or oxygen enriched air (often simply referred to as "air"). Previous studies show that pure oxygen treatment is only slightly better than ambient air at temperatures near 50° C. At higher temperatures (e.g., >80° C.) pure oxygen may have significant advantages over ambient air alone because the nitrogen in the air reduces the partial pressure of oxygen. Lime only treatment without ambient air or oxygen enriched air also significantly increases the enzymatic digestibility of biomass, although not as much as when air is supplied.

Example 2

Preliminary Experiments to Determine Process Conditions and their Effects

Biomass delignification by lime treatment occurs very quickly at high-temperature and high-pressure oxygen conditions (Chang, S. "Lime Pretreatment of Lignocellulosic Biomass", Ph. D. Dissertation, Texas A&M University, May 1999). To determine whether long-term delignification treatment was feasible, an experiment was conducted in which sugarcane bagasse underwent lime pretreatment using air purging at temperatures lower than 60° C.

Figure 18:
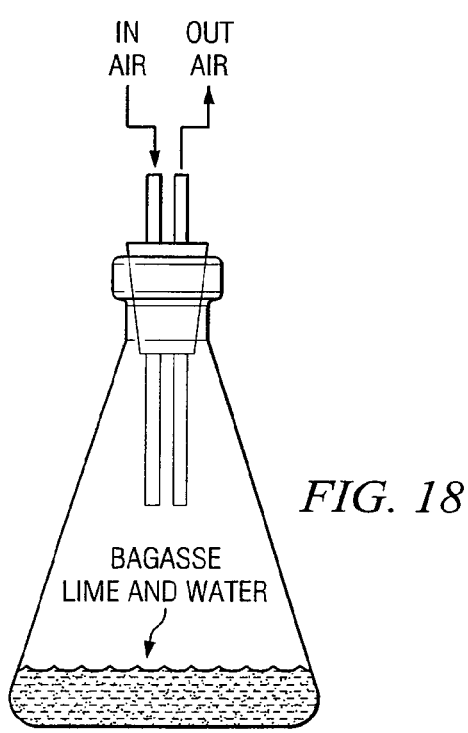
FIG. 18 illustrates an experimental set-up according to an embodiment of the present invention.
Figure 19:
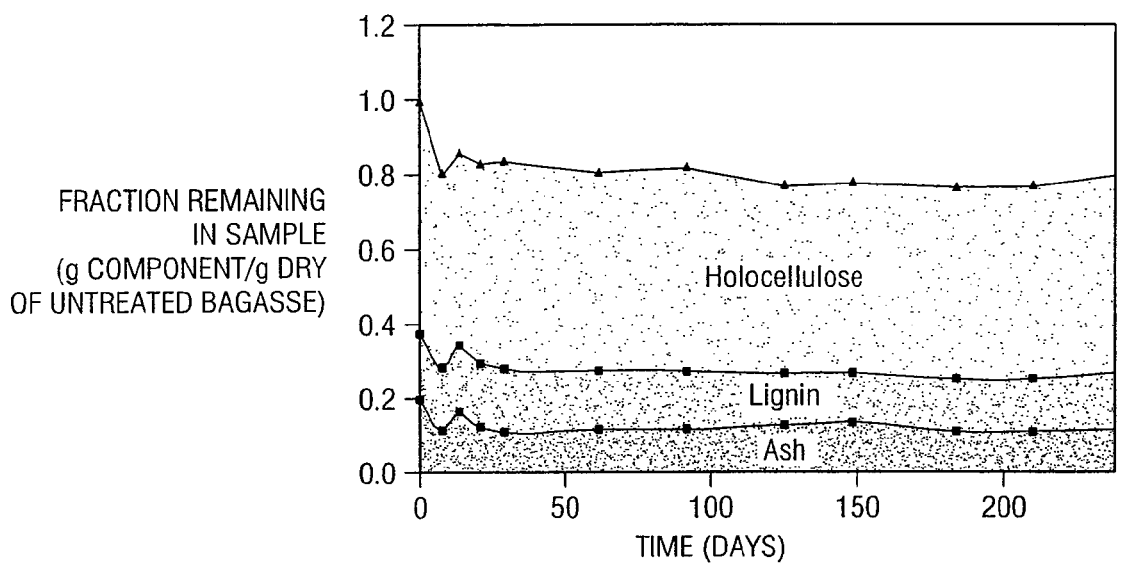
FIG. 19 presents the total mass, holocellulose, lignin and ask for treatment without air purging at 25° C. according to an embodiment of the present invention.
Figure 20:
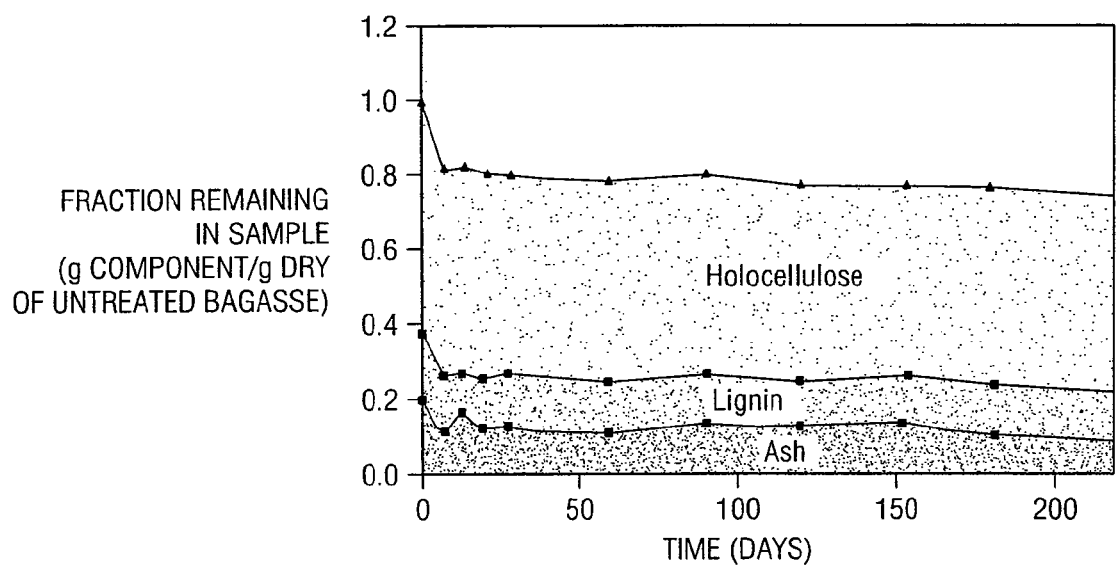
FIG. 20 presents the total mass, holocellulose, lignin and ask for treatment without air purging at 50° C. according to an embodiment of the present invention.
Figure 21:
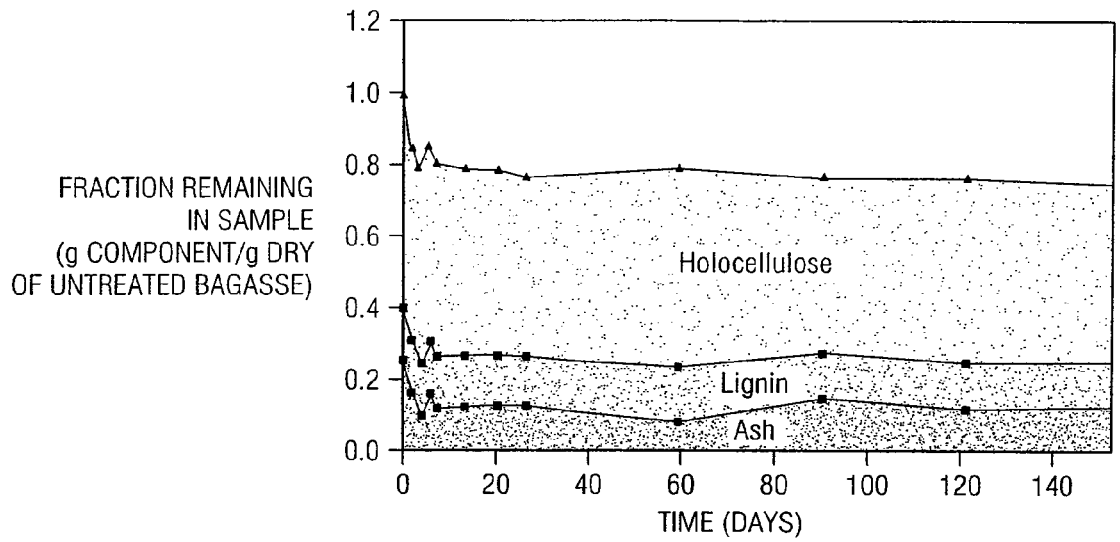
FIG. 21 presents the total mass, holocellulose, lignin and ask for treatment without air purging at 57° C. according to an embodiment of the present invention.
Figure 22:
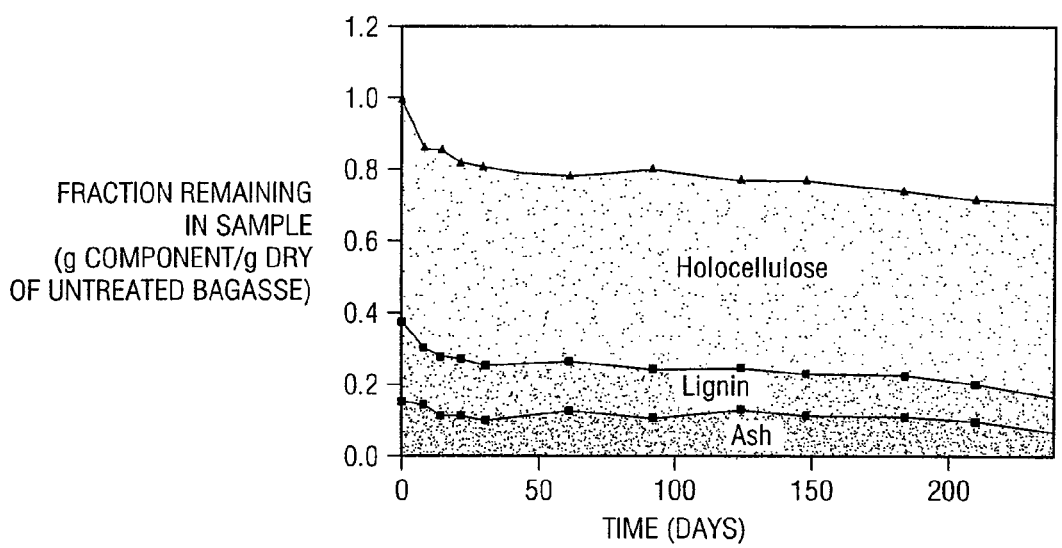
FIG. 22 presents the total mass, holocellulose, lignin and ask for treatment with air purging at 25° C. according to an embodiment of the present invention.

The dry weight of raw sugarcane bagasse (35 mesh) was determined using the NREL Standard Procedure No. 1 (NREL (1992). Chemical Analysis & Testing Standard Procedure, National Renewable Energy Laboratory, Golden, Colo.). Several 125-mL Erlenmeyer flasks were loaded with 3 g dry weight of sugarcane bagasse, 1.5 g of $Ca(OH)_2$ (50% loading) (Fisher Scientific Co.) and 27 mL of distilled water. Several flasks used air as the oxygen source. An equal number of flasks had no air contact and were simply capped as a control. As shown in FIG. 18, the flasks exposed to air were equipped with appropriate 2-hole rubber stoppers through which two glass tubes served as inlet and outlet for the process.

An incubator equipped with a shaker was used to incubate the samples at the following temperatures: 57° C., 50° C. and 25° C. (room temperature). At appropriate times, flasks were removed and analyzed for lignin content, 3-day cellulase enzyme digestibility, total mass loss, and lime consumption. Thus, these parameters were measured as a function of time.

The detailed procedure for the process follows:

400 g of 40-mesh untreated bagasse was placed in several 2 L centrifuge bottles. About 500 mL of water was added to each centrifuge bottle, which were then stirred for about 15 minutes. The bottles were centrifuged at 3500 rpm or more for 5 minutes. As much water as possible was decanted, then the bagasse was re-washed according to the above procedure until the water decanted did not appear to be any clearer than in the previous cycle.

The contents of the centrifuge bottles were transferred into other containers and dried at 45° C. for 24 hours or longer if necessary. The dry biomass was allowed to regain equilibrium moisture content with the environment, which in some cases took several days. After equilibrium was obtained, the moisture content of the sample biomass ($X_1$) was obtained as described in NREL Standard Procedure No. 001.

Several experimental flasks were prepared. Each was filled with 3 g dry weight of the biomass, 1.5 g of $Ca(OH)_2$ and 27 mL of distilled water. The exact amount of biomass ($W_1$) and lime ($W_{initial}$) added to each flask was recorded to the nearest 0.001 g.

Flasks were placed in a shaking incubator at the appropriate experimental temperature. Duplicate flasks were prepared for each set of experimental conditions. These flasks were later divided into identical sample sets A and B. Flasks were removed from the incubator only when necessary to monitor the pretreatment process as described below.

Flasks belonging to sample set A were tested for lime consumption as a function of time. For each flask, after removal from the incubator, the contents were transferred to beaker. As much water as necessary was used to recover as much of the biomass from the flask as possible.

Hydrochloric acid was added to the beaker using a titration apparatus. The buret in the apparatus was filled with a certified standard solution of 1N hydrochloric acid to a starting volume ($V_1$). The biomass solution in the beaker was titrated to a pH of between 6.80 and 7.00. The final volume of HCl ($V_2$) was recorded and used to calculate the amount of line remaining in the biomass sample as follows:

$$W_{remaining} = \frac{1 \text{ mol of } Ca(OH)_2}{2 \text{ mol HCl}} \times \frac{N_{HCl}(V_1 - V_2)}{1000} \times MW$$

where, $W_{remaining}$=Total amount of lime remaining in the biomass sample(g), $N_{HCl}$=Normality of the certified standard HCl solution (mol/L), $V_1$=Starting volume of HCl in titration (mL), $V_2$=Final volume of HCl in titration (mL).

MW=Molecular weight of lime (74.092 g/mol)

Using the exact amount of lime added to the samples before pretreatment ($W_{initial}$) and the amount remaining afterwards $W_{remaining}$, the amount of lime consumed during pretreatment was calculated as follows:

Amount of lime consumed (g/g dry biomass)=$W_{initial}$−$W_{remaining}W_1 \times (1-X_1)$.

The remainder of the biomass was washed as describe above then stored for use in a 3-day enzyme digestibility analysis.

Flasks belonging to sample set B were tested for biomass weight loss due to pretreatment.

After removal of the sample flasks from the incubator, acetic acid was added to each to reduce the pH to approximately 5-6 and solubilize any unreacted lime. The contents of each flask was then transferred to a 2 L centrifuge bottle, using as much water as necessary to ensure transfer of as much treated biomass as possible. The centrifuge bottle was then filled with water and stirred for 15 minutes. Next the water/biomass mixture was centrifuged at 3500 rpm or more for 5 to 10 minutes.

A vacuum filtration apparatus using a Buchner funnel and a predried preweighed filter paper was prepared. As much water was possible was decanted from the centrifuged samples into the vacuum filtration apparatus. The washing and filtering process was repeated until the filtrate became clear. Filter papers were replaced as necessary.

After washing, as much biomass as possible, using as much water was necessary, was transferred to a beaker. The biomass and all filter papers used during its washing were dried at 45° C. for 24 hours or longer. The biomass and filters were then cooled in a desiccator until they reached room temperature. Then the net weight of the biomass was obtained ($W_2$).

Immediately after weighing, about 0.5 g of the dried biomass was used to determine the moisture content ($X_2$) as described in the NREL Standard Procedure No. 001. The remainder of the biomass was stored for use in a 3-day enzyme digestibility analysis.

The total weight loss due to pretreatment was calculated using the following formula:

Total Weight Loss %=$W_1 \times (1-X_1) - W_2 \times (1-X_2)W_1 \times (1-X_1)$ where, $W_1$=Weight of the washed raw biomass before pretreatment in each flask (g), $X_1$=Moisture content of the washed raw biomass at room temperature (g $H_2O$/g total weight), $W_2$=Weight of the dried biomass, and $X_2$=Moisture content of the dried biomass ($W_2$).

Remaining biomass from matching flasks of sample sets A and B were combined for a 3-day enzyme digestibility analysis.

The Klason lignin content of the pooled samples was determined using NREL Standard Procedure No. 003. Using the same procedure, the ash content in the biomass was also determined. Assuming that baggase is composed only of lignin, ash, and holocellulose, the holocellulose content was also obtained by subtracting ash and lignin contents from 100%.

The procedure used for the 3-day digestibility studies was identical to the procedure in Sushien Chang's dissertation (Texas A&M University, 1999) under the title "Enzymatic Hydrolysis Procedure for Fundamental Studies of Lime Pretreatment."

In the standard analysis procedure, 2.5 g dry weight biomass is used as a sample. If other weights were used, normally because 2.5 g of biomass was not available after pretreatment, amounts of all reagents were adjusted in proportion to the actual amount of biomass.

The final samples were analyzed for glucose and xylose concentration using an HPX-87P carbohydrate HPLC column (Biorad Laboratories). The final results were reported in grams of sugar yielded (glucose+xylose) per gram dry weight of untreated biomass. This data may be obtained from the raw glucose and xylose concentration data by multiplying the result, which is in grams of sugar yielded per gram dry weight of treated biomass by the dry weight of biomass remaining after washing ($W_1 \times (1-X_2)$) and then dividing by the total dry weight of untreated biomass ($W_1 \times (1-X_1)$).

This procedure assumes that any water-soluble substances resulting from the pretreatment are not digestible by cellulase enzyme.

FIGS. 19 to 28 depict the total mass, holocellulose, lignin and ash in each sample treated and analyzed as described above as function of time.

Figure 23:
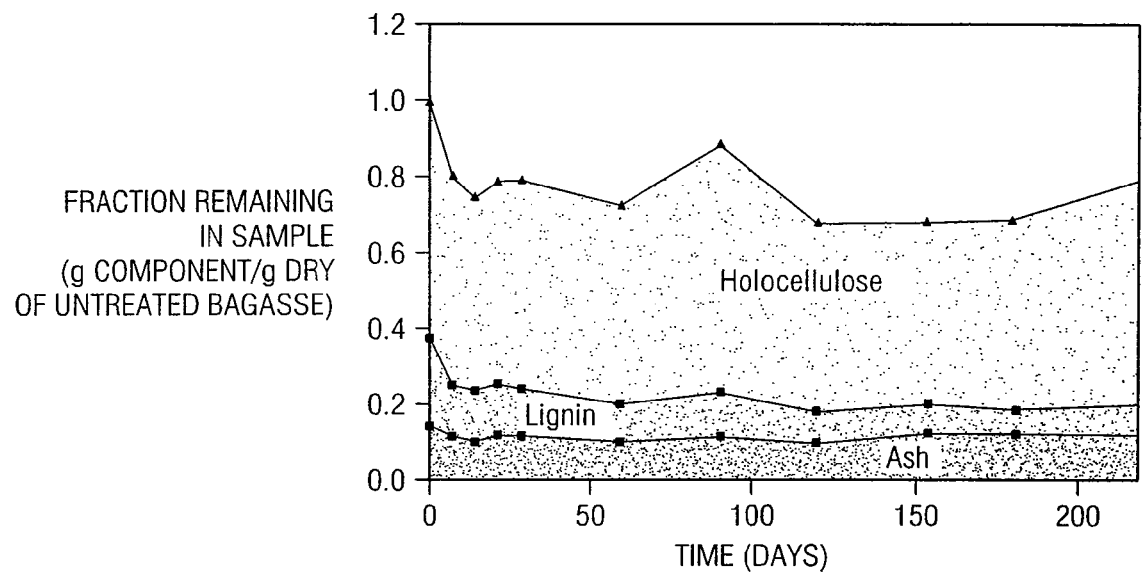
FIG. 23 presents the total mass, holocellulose, lignin and ask for treatment with air purging at 50° C. according to an embodiment of the present invention.
Figure 24:
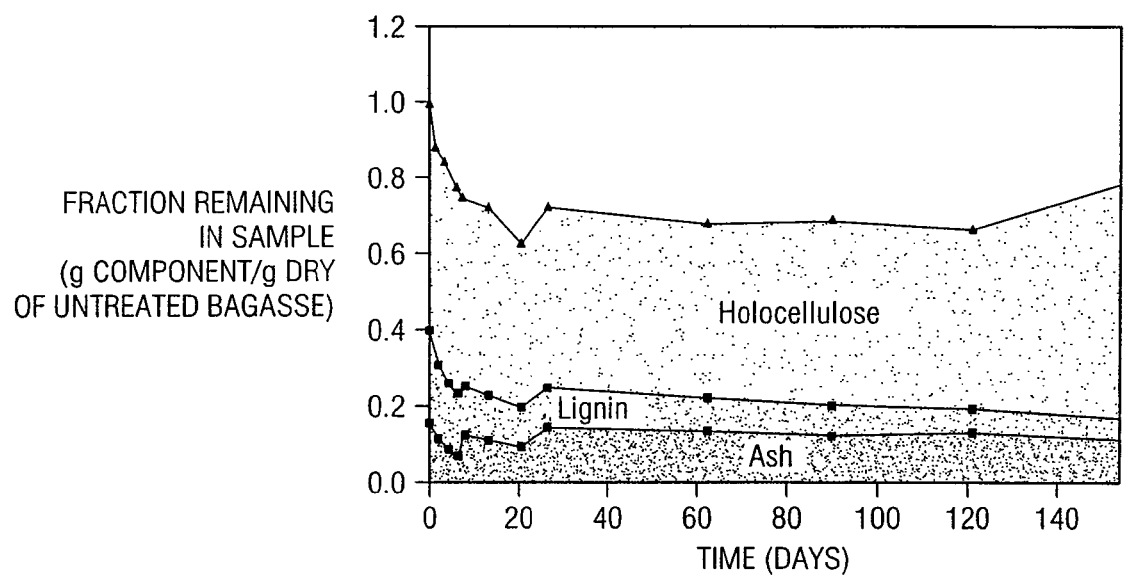
FIG. 24 presents the total mass, holocellulose, lignin and ask for treatment with air purging at 57° C. according to an embodiment of the present invention.
Figure 25:
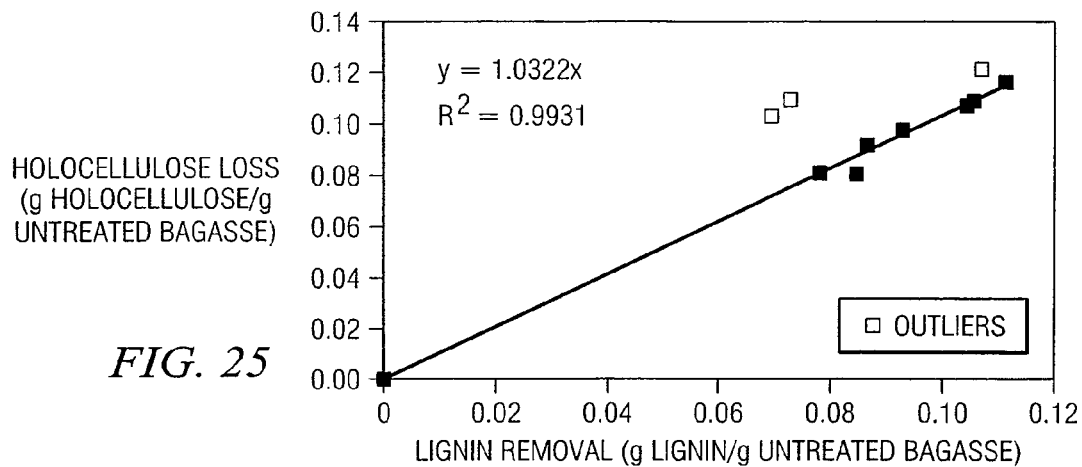
FIG. 25 presents holocellulose loss as a function of lignin removal for lime pretreatment of bagasse without air purging at 25° C. according to an embodiment of the present invention.
Figure 26:
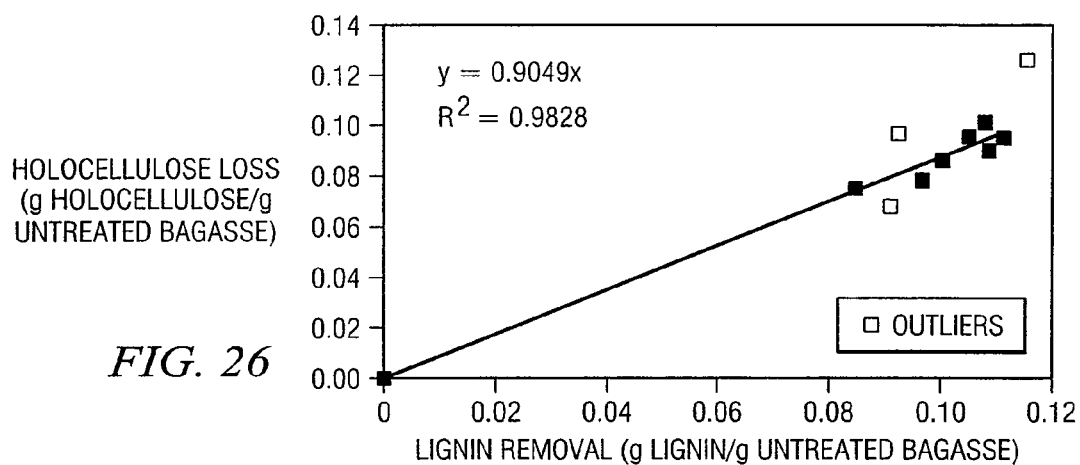
FIG. 26 presents holocellulose loss as a function of lignin removal for lime pretreatment of bagasse without air purging at 50° C. according to an embodiment of the present invention.
Figure 27:
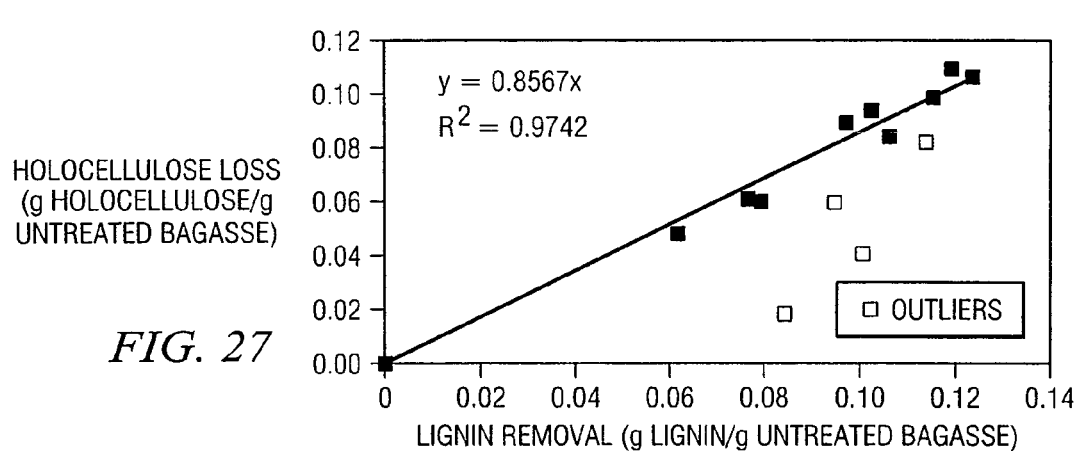
FIG. 27 presents holocellulose loss as a function of lignin removal for lime pretreatment of bagasse without air purging at 57° C. according to an embodiment of the present invention.
Figure 28:
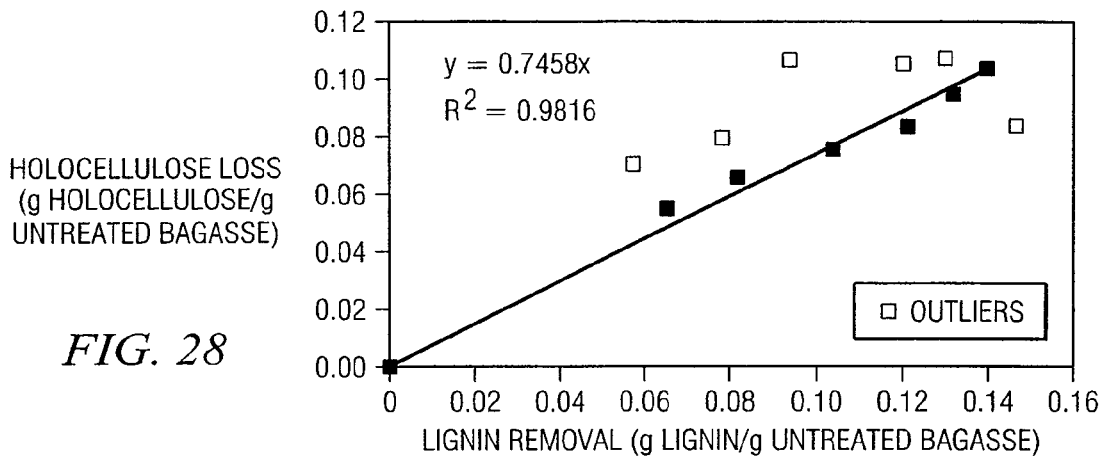
FIG. 28 presents holocellulose loss as a function of lignin removal for lime pretreatment of bagasse with air purging at 25° C. according to an embodiment of the present invention.
Figure 29:
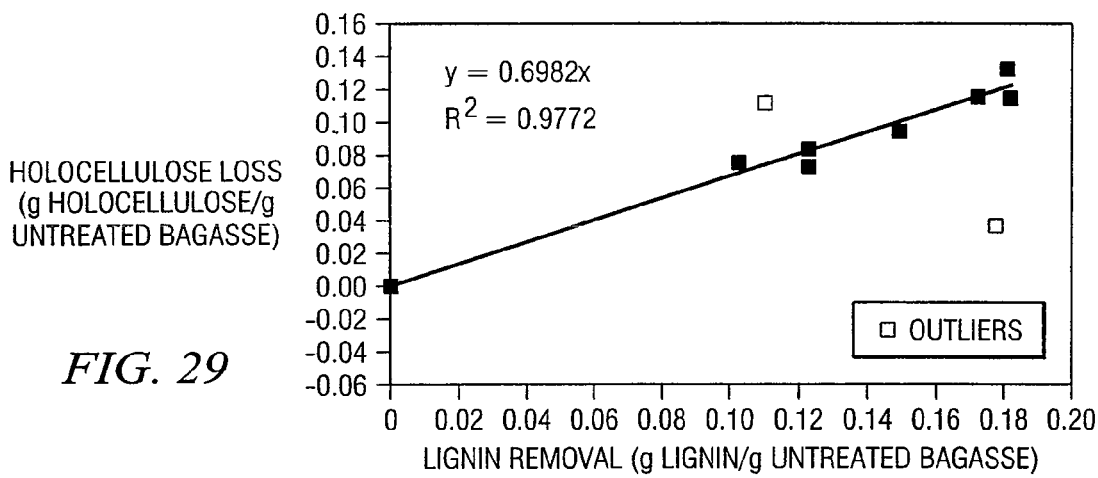
FIG. 29 presents holocellulose loss as a function of lignin removal for lime pretreatment of bagasse with air purging at 50° C. according to an embodiment of the present invention.
Figure 30:
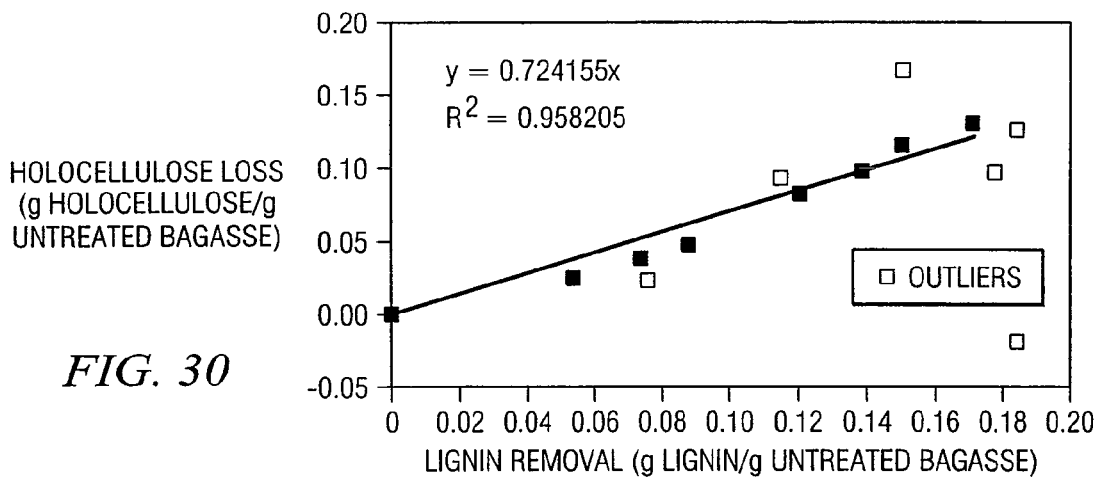
FIG. 30 presents holocellulose loss as a function of lignin removal for lime pretreatment of bagasse with air purging at 57° C. according to an embodiment of the present invention.
Figure 31:
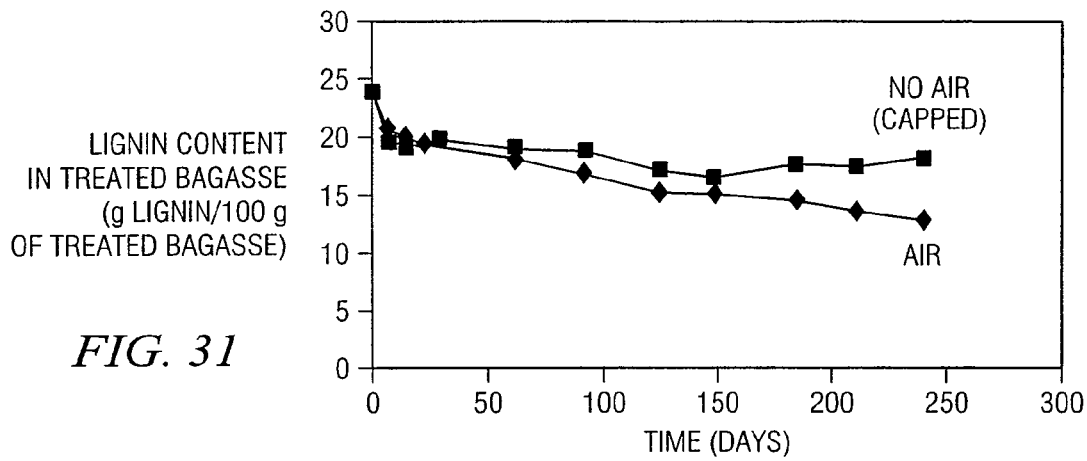
FIG. 31 presents the lignin content in lime-treated bagasse (25° C.) according to an embodiment of the present invention.
Figure 32:
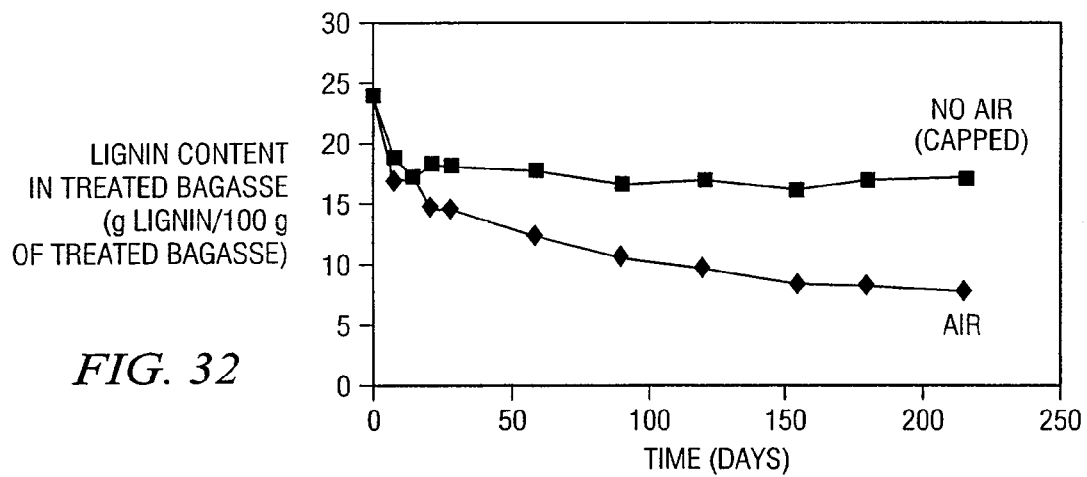
FIG. 32 presents the lignin content in lime-treated bagasse (50° C.) according to an embodiment of the present invention.

FIGS. 23-28 show that, for all experimental conditions in which lime is supplied, there is a rapid decrease of holocellulose and lignin in the first 7 days. After the first 7 days, the material loss begins to level off. A more rapid material loss was observed if the temperature was higher (FIGS. 25 and 28).

In the samples without air purging, after the initial material loss, no significant loss occurred (FIGS. 23, 24 and 25). In samples subjected to air purging (FIGS. 26, 27 and 28), material loss continues, although the rate of degradation is lower than during the first month. Also, selective lignin removal can be observed in these samples, with a more rapid removal at higher temperatures.

Selective lignin removal is significant because it describes the effectiveness of some embodiments of the present invention. Ideally, a good delignification process should remove lignin without a significant loss of holocellulose.

FIGS. 29 to 34 show holocellulose loss as a function of lignin removed.

The slopes from the linear regressions in FIGS. 29 to 34 indicate the selectivity of the process. The selectivity, defined as g of holocellulose lost/g of lignin removed, is ideally as low as possible. Table 1 presents the selectivities (slopes) of the linear regressions from FIGS. 29 to 34

TABLE 1

Selectivity of holocellulose loss against lignin removal (g holocellulose/g lignin)

| Temp. (° C.) | ±(95% C.I.) | No Air | ±(95% C.I.) | Air |
|---|---|---|---|---|
| 25 | 1.032 | 0.078 | 0.746 | 0.112 |
| 50 | 0.905 | 0.107 | 0.698 | 0.096 |
| 57 | 0.857 | 0.110 | 0.724 | 0.151 |

C.I. = Confidence Interval

The results of the experimental samples not provided with air suggest that the selectivity decreases with temperature. In the case of experimental samples provided with air it appears that there is no difference in selectivity based on temperature. When comparing the samples provided with and air and those without air that were incubated at the same temperature, the 95% confidence intervals suggest that the selectivity is smaller (better), for the samples provided with air for both 25° C. and 50° C., but there is no significant difference for 57° C.

FIGS. 35-39 present lignin content of the experimental samples, expressed as g of lignin remaining/100 g of treated bagasse.

Figure 34:
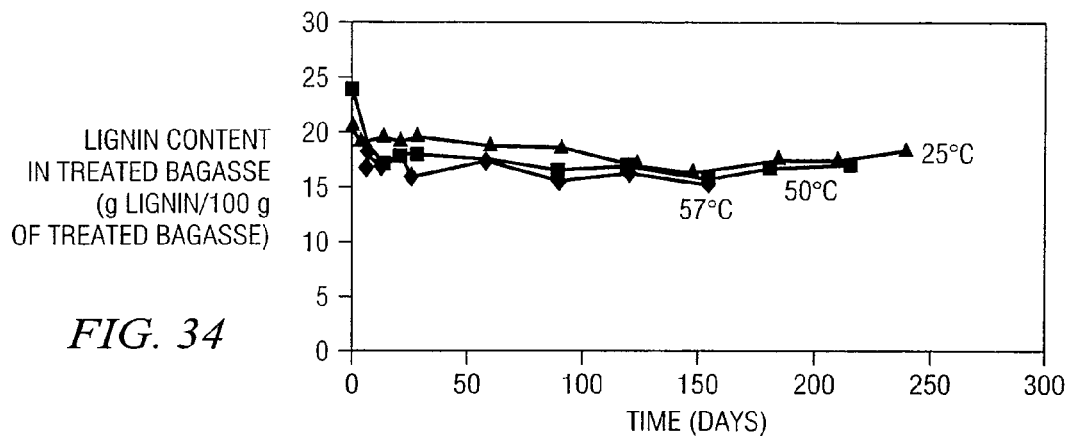
FIG. 34 presents the lignin content in bagasse lime-treated without air purging according to an embodiment of the present invention.
Figure 35:
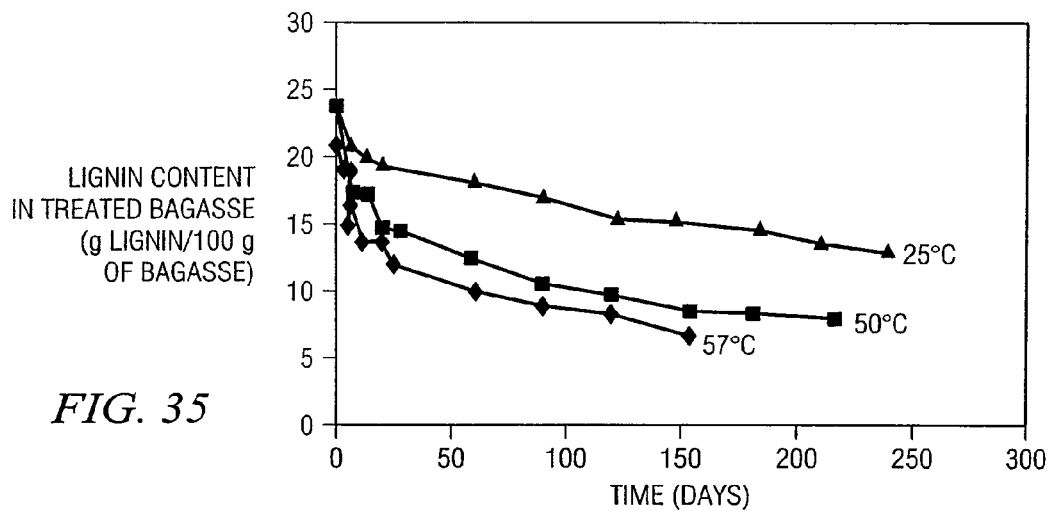
FIG. 35 present the lignin content in bagasse lime-treated with air purging according to an embodiment of the present invention.
Figure 36:
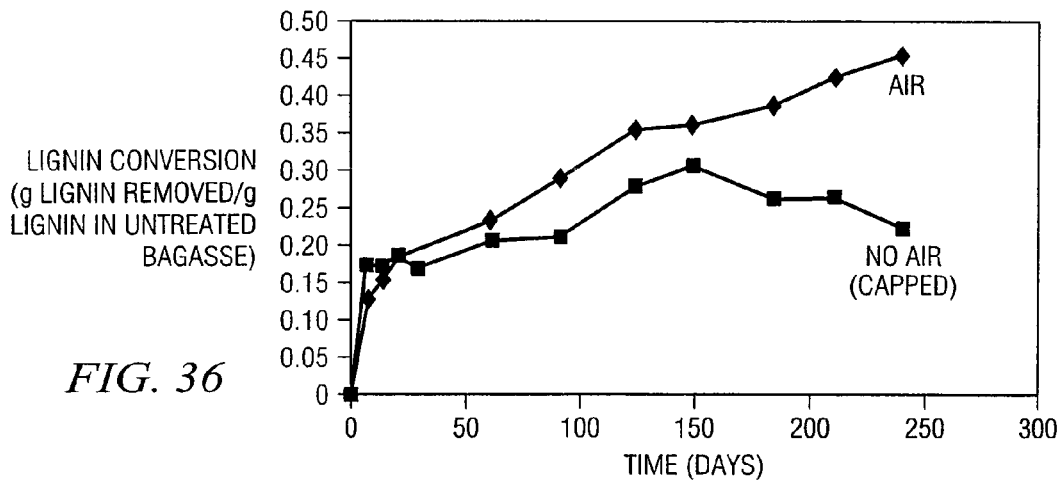
FIG. 36 presents the lignin conversion of lime-treated bagasse at 25° C. according to an embodiment of the present invention.
Figure 37:
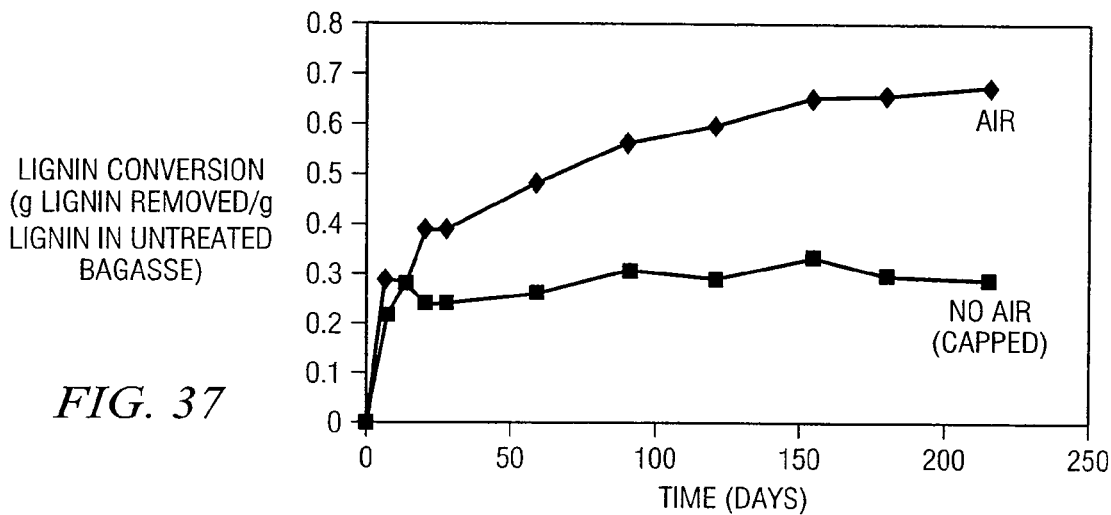
FIG. 37 presents the lignin conversion of lime-treated bagasse at 50° C. according to an embodiment of the present invention.
Figure 38:
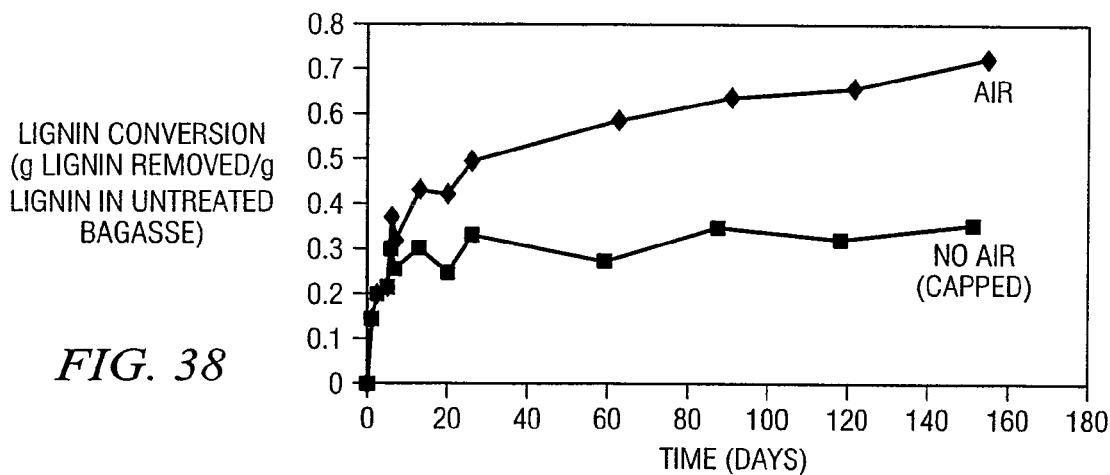
FIG. 38 presents the lignin conversion of lime-treated bagasse at 57° C. according to an embodiment of the present invention.
Figure 39:
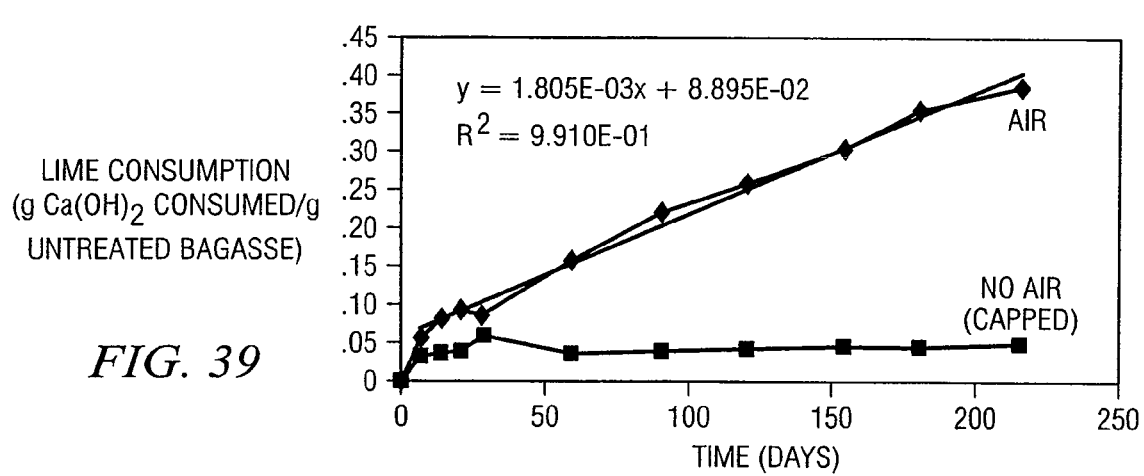
FIG. 39 presents the lime consumed in treatment of bagasse at 50° C. according to an embodiment of the present invention.

FIGS. 36-39 suggest that delignification is directly related to temperature and the presence of oxygen. FIGS. 36 and 37 show that delignification was more pronounced when oxygen was present. FIG. 34 shows that when oxygen is not present, temperature does not have a significant effect on delignification. On the other hand, in FIG. 35, where oxygen was present, delignification decreased with temperature.

Figure 33:
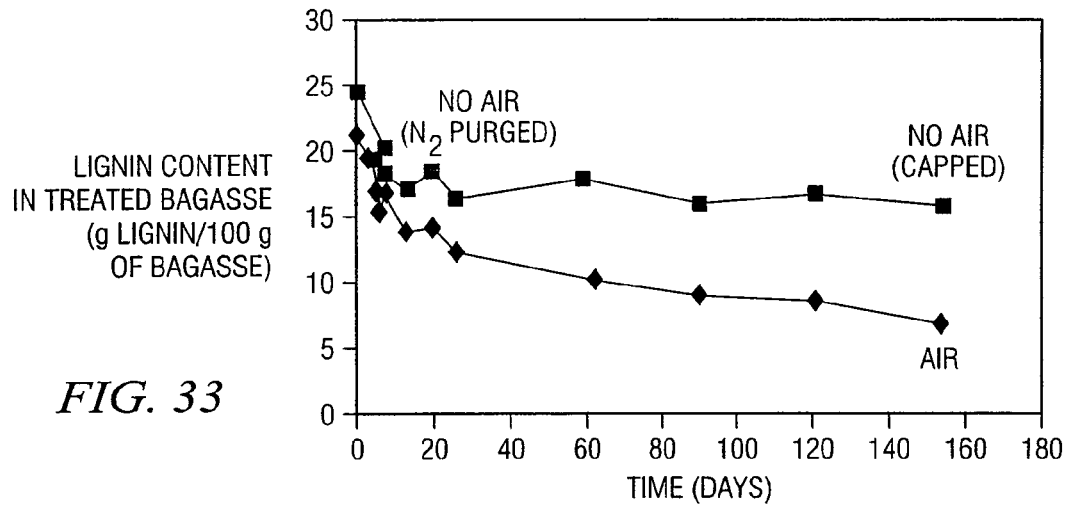
FIG. 33 presents the lignin content in lime-treated bagasse (57° C.) according to an embodiment of the present invention.

Even when there is no oxygen present (FIGS. 36-38), delignification occurs very rapidly during the first week and continues to level off after about a month. Because the samples that were not provided with air were in capped bottles, these bottles contained a head of air, which could provide some oxygen and give a high delignification rate during the first week. To test this hypothesis, a sample was first purged with nitrogen for 10 minutes and then capped. The result is shown in FIG. 33. Delignification rate of the purged samples was similar to the capped bottle samples, indicating that the small amount of oxygen in the head space of capped bottles is insignificant. Therefore, it is likely that some of the lignin in the bagasse is labile to lime alone and does not require oxygen for its degradation.

Another way of analyzing lignin removal is by examining the fraction of lignin removed or lignin conversion as a function of time, which is computed as follows:

$$\text{Lignin Conversion} = L_0 - L_t / L_0,$$

where $L_0$=lignin content at time 0, and $L_t$=lignin content at time t.

Figure 40:
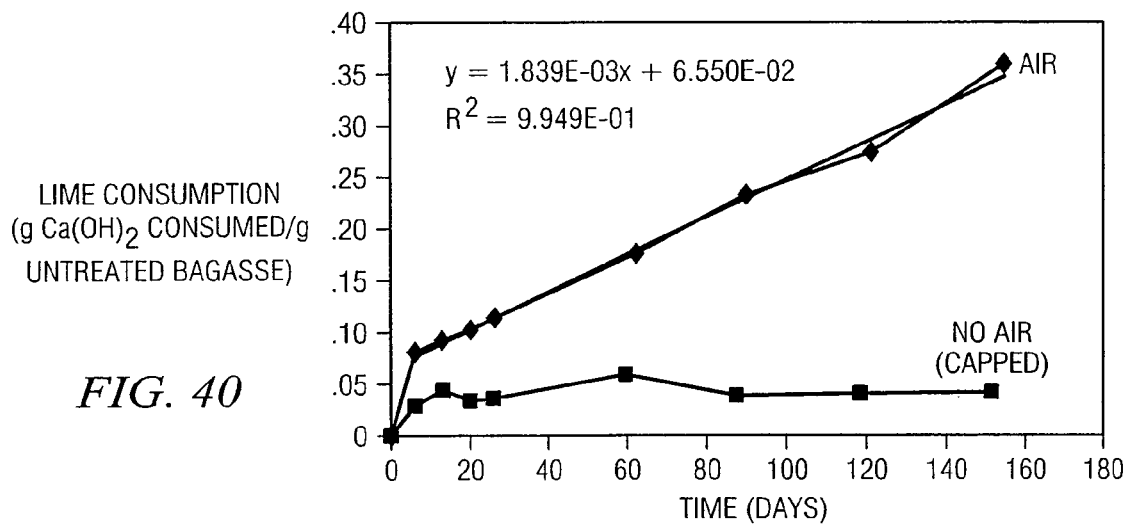
FIG. 40 presents the lime consumed in treatment of bagasse at 57° C. according to an embodiment of the present invention.
Figure 41:
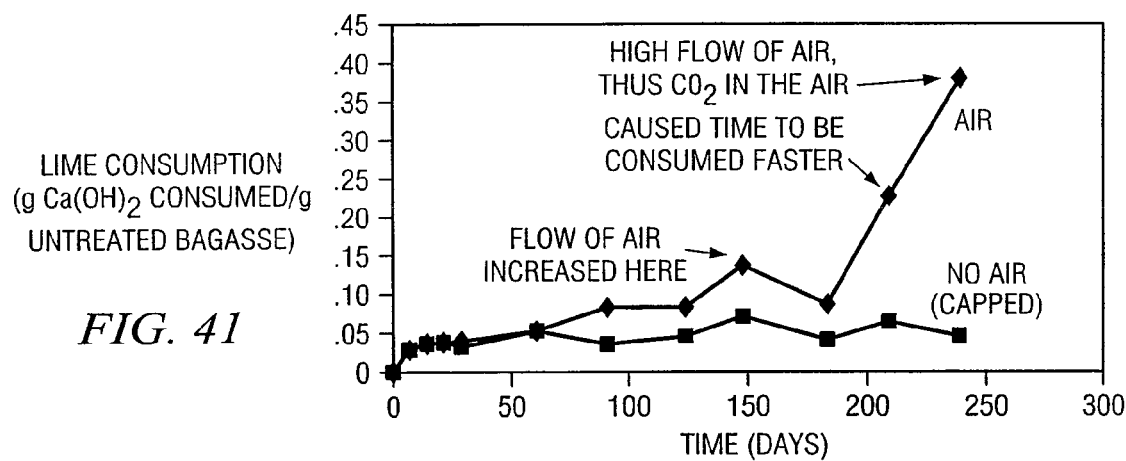
FIG. 41 presents the lime consumed in treatment of bagasse at 25° C. according to an embodiment of the present invention.
Figure 42:
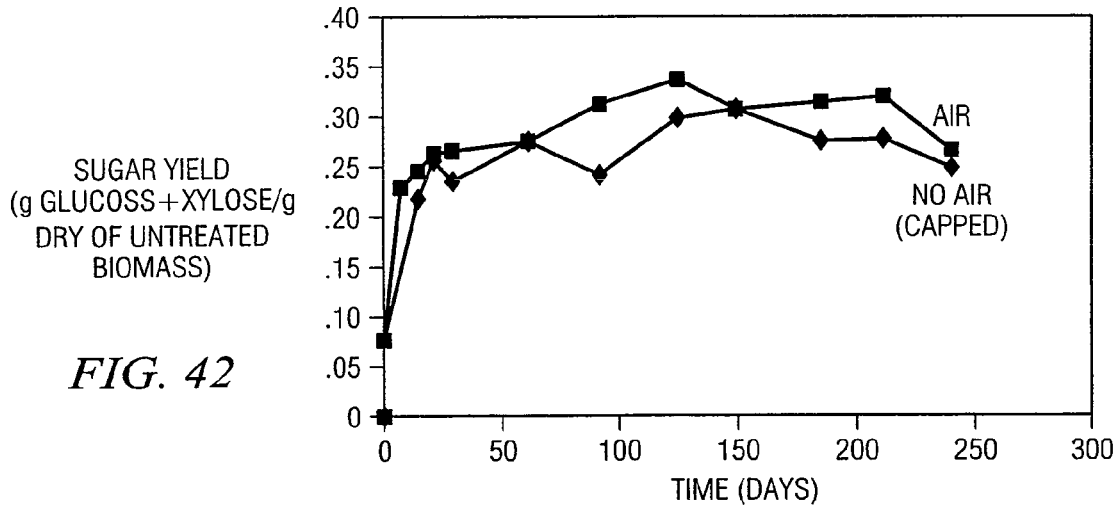
FIG. 42 presents the 3-day enzyme digestibility of bagasse treated at 25° C. according to an embodiment of the present invention.

FIGS. 40-42 show that without air, lignin conversion is only 20 to 30%, whereas with air purging, lignin conversion increases significantly at higher temperatures to over 70%.

Figure 43:
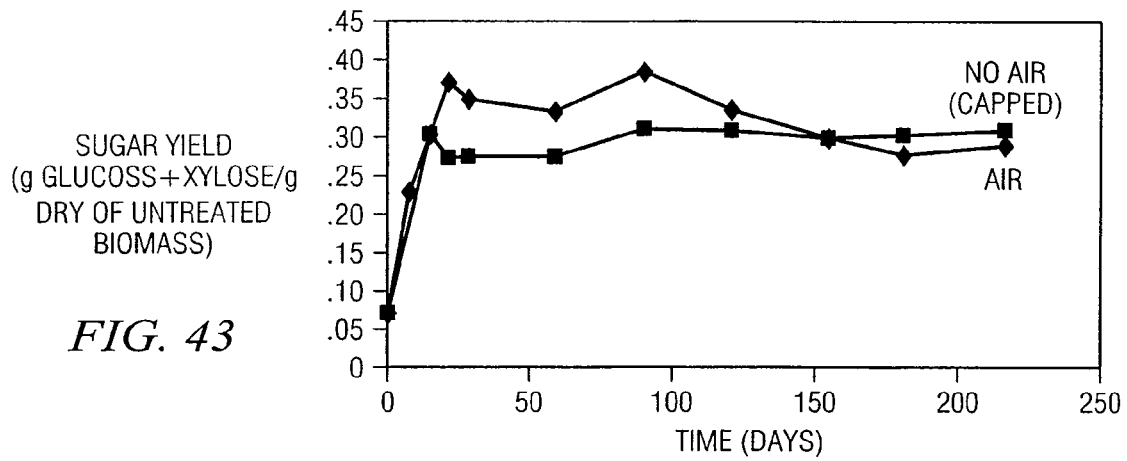
FIG. 43 presents the 3-day enzyme digestibility of bagasse treated at 50° C. according to an embodiment of the present invention.
Figure 44:
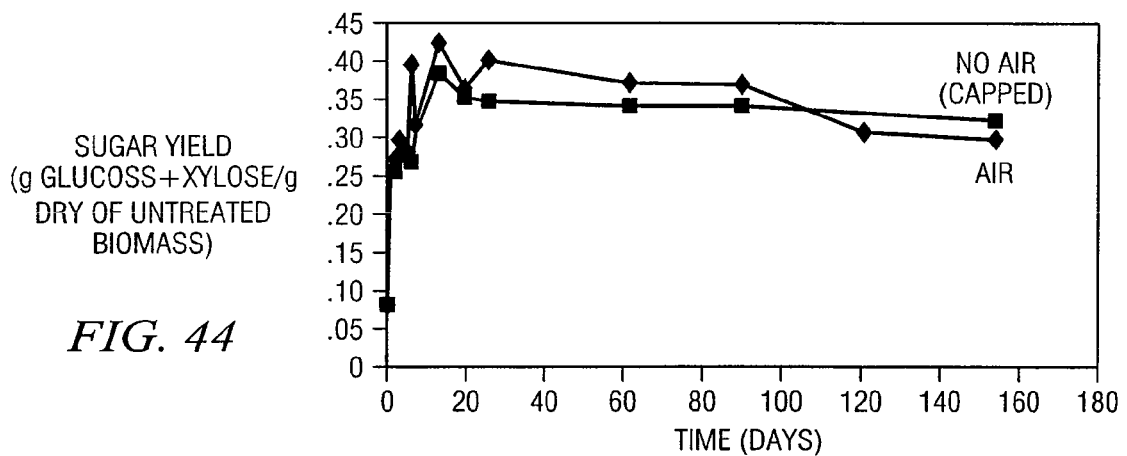
FIG. 44 presents the 3-day enzyme digestibility of bagasse treated at 57° C. according to an embodiment of the present invention.
Figure 45:
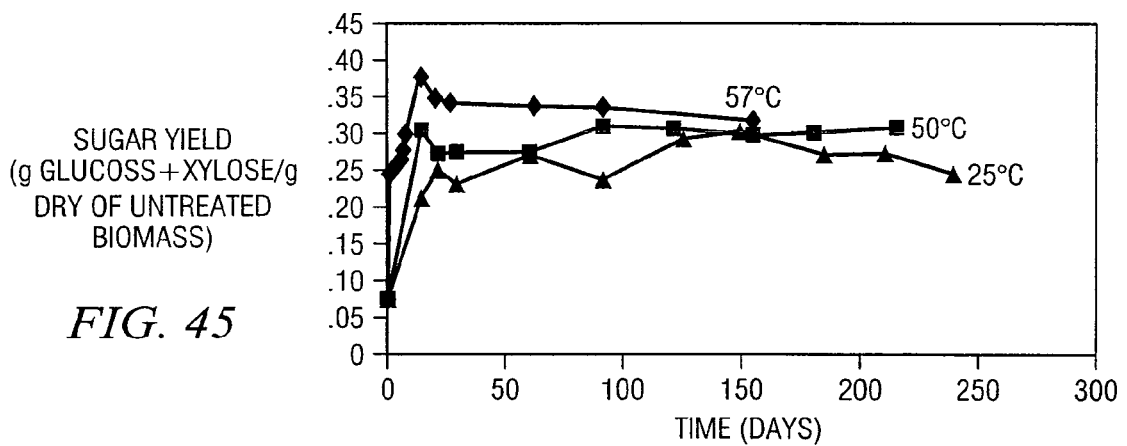
FIG. 45 presents the 3-day enzyme digestibility of bagasse treated without air according to an embodiment of the present invention.

FIGS. 43-45 show the estimated lime consumption during biomass pretreatment. Those samples that were subject to air purging were exposed to carbon dioxide in the air. Because the pretreatment takes several months to complete, the amount of carbon dioxide that reacts with the lime was significant, thus the lime consumption obtained in this experiment is an overestimate. The avoid this higher lime consumption, the air may be scrubbed to remove carbon dioxide prior to addition to the biomass.

FIGS. 43 and 44 show that the consumption of lime as a function of time is linear at experimental temperatures of 50° C. and 57° C. The slopes of the curves were $1.606 \times 10^{-3} \pm 0.125 \times 10^{-3}$ (95% confidence interval) g of Ca(OH)$_2$/(g of untreated biomass·day) for the treatment at 50° C. and $1.839 \times 10^{-3} \pm 0.132 \times 10^{-3}$ (95% confidence interval) g of Ca(OH)$_2$/(g of untreated biomass·day) for the treatment at 57° C.

The experiments without addition of air did not show any significant lime consumption after the first week.

In FIG. 41, it can be observed that the consumption of lime in the biomass sample climbed significantly after the flow of air was increased, showing that the carbon dioxide in the air did consume the lime.

Iogen cellulase enzyme (Iogen Laboratories), with an average activity of 67.9 FPU/mL, was used to run 3-day cellulase enzyme digestibility. (See FIGS. 46-50).

Figure 46:
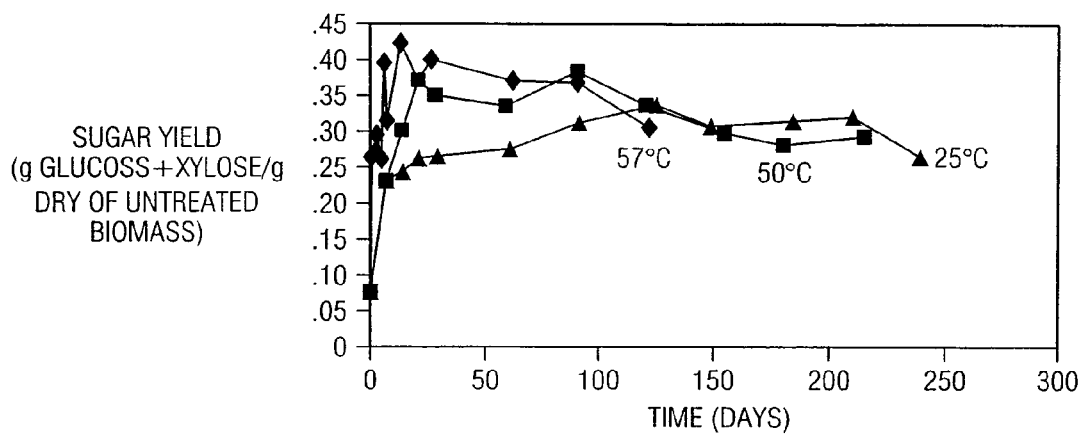
FIG. 46 presents the 3-day enzyme digestibility of bagasse treated under air purging according to an embodiment of the present invention.
Figure 47:
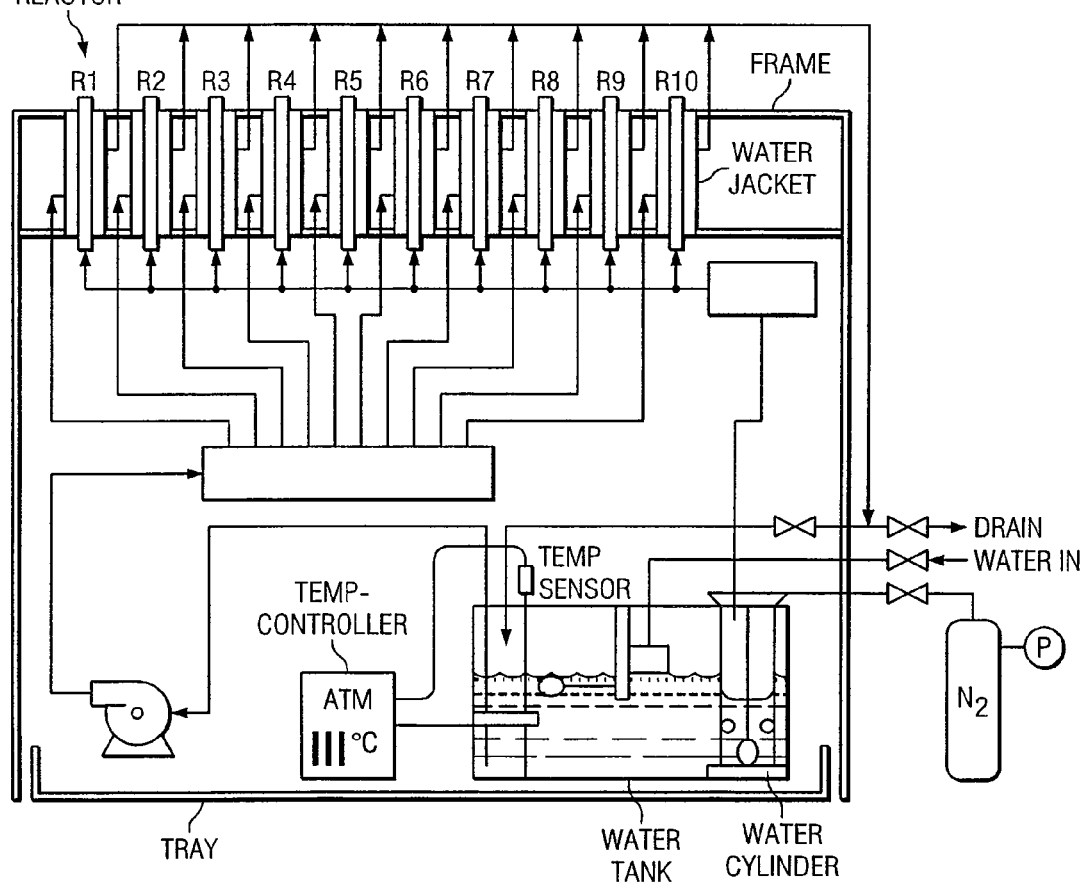
FIG. 47 illustrates a subset of a jacketed reactor system for non-oxidative lime pretreatment ($N_2$ supply) according to an embodiment of the present invention.
Figure 48:
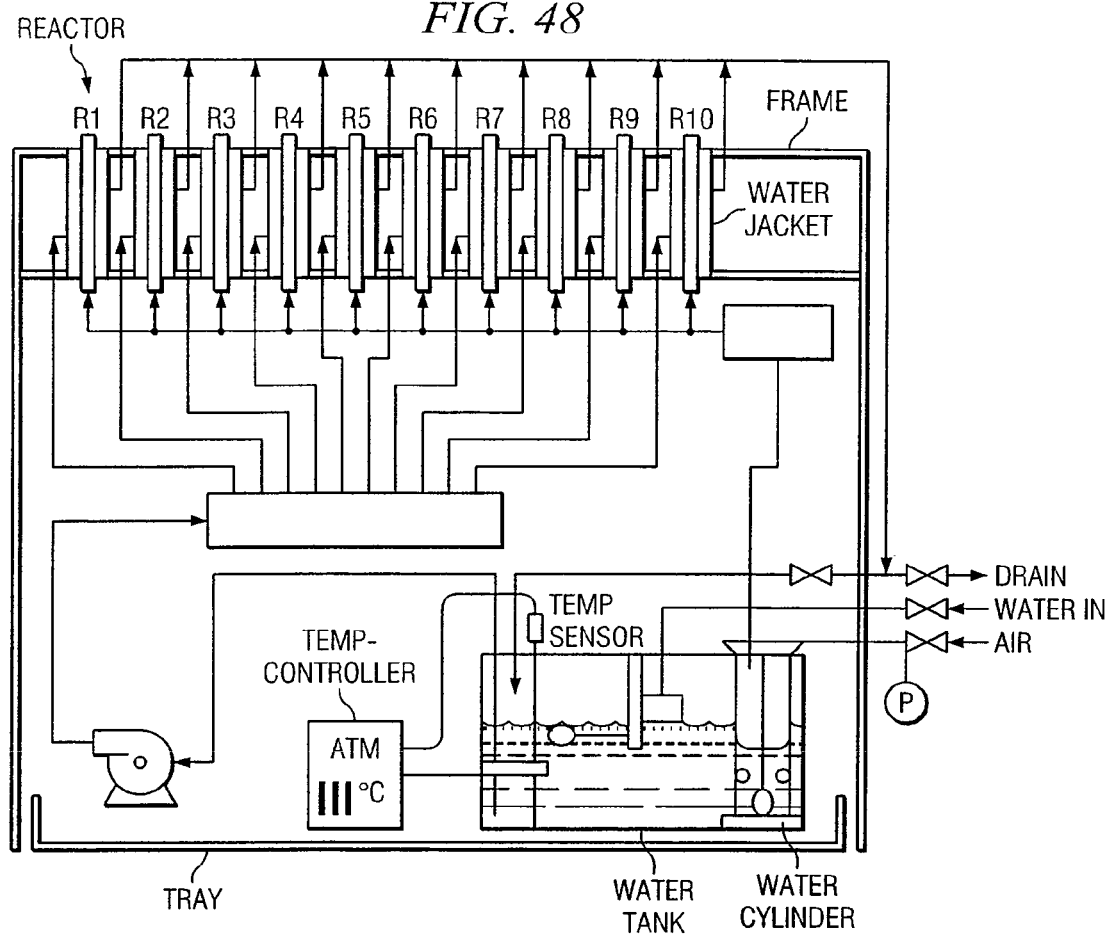
FIG. 48 illustrates a subset of a jacketed reactor system for non-oxidative lime pretreatment (air supply) according to an embodiment of the present invention.
Figure 49:
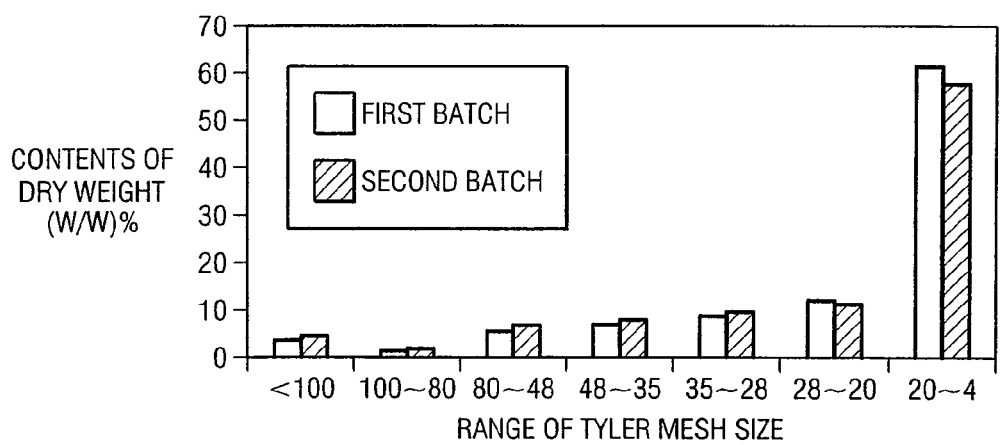
FIG. 49 presents the particle size distribution of the first and second batches of corn stove processed according to an embodiment of the present invention.
Figure 50:
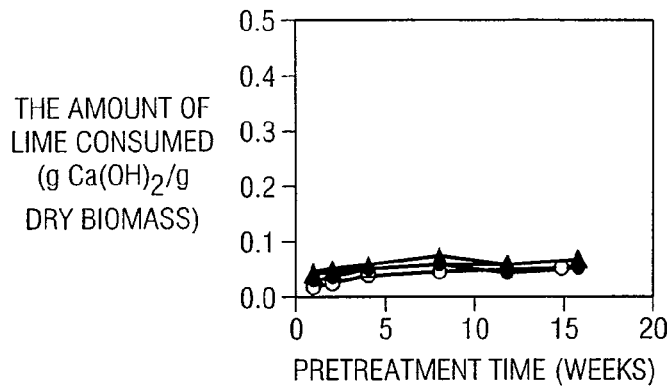
FIG. 50 presents profiles of lime consumption for non-oxidative pretreatment at 25, 35, 45 and 55° C. according to an embodiment of the present invention.

FIGS. 46 to 48 show that to enhance enzymatic digestibility, pretreatment after 14 to 21 days is unnecessary. FIGS. 49 and 50 show that higher temperatures achieve higher conversions, even for the samples without added air (FIG. 46).

Example 3

General Conditions and Methods

The following conditions and methods were used in the experiments of Example 4 and may be readily adapted by one of skill in the art to determine other suitable embodiments of the present invention.

Particle Size Distribution of Raw Biomass
Sieves
USA standard testing sieves (A.S.T.M.E.-11 Specification)

TABLE A

Specification of Sieves

| Sieve number Mesh | Tyler Equivalent mm | Opening size in |
|---|---|---|
| 4 | 4 | 4.750 | 0.1870 |
| 20 | 20 | 0.850 | 0.0331 |
| 30 | 28 | 0.600 | 0.0234 |
| 40 | 35 | 0.425 | 0.0165 |
| 50 | 48 | 0.300 | 0.0117 |
| 80 | 80 | 0.180 | 0.0070 |
| 100 | 100 | 0.150 | 0.0059 |

Procedures 50 g dry biomass was loaded on the sieve of mesh No. 100. The lid, bowl and seive apparatus was vigorously shaken in a horizontal plane for 1 minute. The particles collected in the seive were stored. Particles in the bowl where transferred to a seive of lower mesh number and the process was repeated until mesh No. 4 was reached. All samples from seives were dried at 105° C. for 24 hours, then weighed to determine dry weight for particles collected by each seive size.

Lime Pretreatment

Lignocellulosic substrate was pretreated with lime in the presence of water. Four sets of packed bed PVC columns (D×L=1 inch×17 inches) were used for the lime-pretreatment reaction at 25 (ambient temperature), 35° C., 45° C., and 55° C. Each set included two subsets, one with and one without aeration to achieve oxidation and non-oxidation conditions, respectively. The total number of columns for each subset is 10 in order to allow analysis at five different run-times. Three sets of columns with water jackets were operated at three different temperatures, 35° C., 45° C., and 55° C., by the water heating and circulating system.

The water heating and circulating system had two parts: a temperature controller and a water circulator. (See FIGS. 51 and 52.) The temperature controller contained a temperature controller (1/16 DIN, OMEGA), a thermocouple (KTSS-18G-18, OMEGA), a heating element (1.5 kW, 120 V), a solid-state relay (RSSDN-25A, Idec Co.), fuses (12.5 A and ¼ A), and a main switch. The water circulator contained a centrifugal pump (¾ HP, TEEL), a water tank (8 gal, Nalgene Co., USA), a manifold having one input and 20 output fittings, and return pipelines.

Air supplied by the Carter-Mattil compressor was preheated and saturated in the cylinder within the water tank and then distributed to each column by the air-manifold having one input and ten output fittings. Compressed nitrogen gas (Plaxair Co., College Station, Tex.) was used to make the non-oxidation condition and supplied to each column by the N2-manifold after preheating and saturation. (See FIG. 47.)

Fill water into the water tank over the level of the heating element. Turn on the centrifugal pump to circulate water. Fill sufficient water into the tank up to top level.

For pretreatment, water was placed in the water tank to cover the heating element. The centrifugal pump was activated to circulate the water and then the tank was filled to top level. The temperature controller was used to heat water to the selected pretreatment temperature and the entire heating and circulating system was allowed to reach a steady state. (This was not required for pretreatments at ambient temperature.)

Raw biomass (15.0 g dry weight of corn stover), lime (7.5 g dry weight), and distilled water (150 mL) were transferred into the reactor after thoroughly being mixed using a spatula.

The biomass mixture was transferred to the reactor, which was tightly capped. A bubble indicator filled with 20-25 mL of distilled water in a 50 ml plastic tube was used to measure the gas flow rate.

A main valve was slowly opened to supply either nitrogen for non-oxidation pretreatment or air for oxidation pretreatment separately. Bubble formation was confirmed in the bubble indicator. The gas flow rate was adjusted to 1 bubble/second using a clamp, which was placed at the air intake tube in the bottom of the reactor.

Gas pressure (4.5-5.0 psi in case of nitrogen gas and 60-80 psi in case of in-line air) was regularly checked as was gas flow rate, seals, water levels in the cylinder filled with water and in the tank, and working temperatures.

After the pretreatment time elapsed, the reactors were moved out of the system and cooled down to ambient temperature. Samples were then removed for various analyses.

Biomass Washing Procedure

Washing and measurement procedures and mass calculations for untreated and treated biomass were performed in a substantially similar manner to that in Example 2.

Enzyme Hydrolysis

Lime-pretreated and washed biomass was transferred from the reactors to tubes with distilled water. Citrate buffer (1.0 M, pH 4.8) and sodium azide solution (1 (w/w) %) were added to the slurry to keep constant pH and prevent microbial growth, respectively. Glacial acetic acid or saturated sodium hydroxide solution was then added to adjust the pH to approximately 4.8. The total volume of mixture was then increased to the desired volume by adding distilled water. The tube was placed in a rotary shaker at 100 rpm and 50° C. After 1-hour incubation, cellulase (NREL, USA) and cellobiase (Novozyme 188, activity=~250 CBU/g) were added to the test tube. The loading rate of cellulase was 0, 1, 5, 10, 20, or 60 FPU/g dry biomass and that of cellobiase was 28.5 CBU/g dry biomass. Samples were withdrawn at 0, 1, and 72 hours and sugars were measured at each time point. The same procedure was also applied to untreated biomass.

Sugar Measurement

Reducing sugar was measured using the dinitrosalicylic acid (DNS) assay (Miller, 1959). A glucose standard prepared from the Sigma 100 mg/dL glucose standard solution was used for the calibration, thus the reducing sugars were measured as "equivalent glucose".

Example 4

Treatment of Corn Stover

Because raw corn stover has a broad particle size distribution, the particle size distributions in the two batches of corn stover used in this example were compared to identify any batch to batch variation.

To compare particle sizes in the corn stover, the batches were sieved with USA standard testing sieves, which are well known in the art.

During the sieving, about 3.0 (w/w) % dry weight of corn stover was lost. The portion of large size particle, Tyler Mesh No. 28~4, of the second batch corn stover was about 4.0 (w/w) % smaller than that of the first batch corn stover (See Table 2).

TABLE 2

The particle size distribution of the first and second batches of corn stover

| Range of Tyler Mesh Size | Weight Contents (w/w) % | | |
|---|---|---|---|
| | First Batch | Second Batch | Difference* |
| <100 | 3.75 | 4.49 | 0.73 |
| 100~80 | 1.35 | 1.80 | 0.45 |
| 80~48 | 5.68 | 6.84 | 1.16 |
| 48~35 | 6.95 | 7.95 | 0.99 |
| 35~28 | 8.68 | 9.44 | 0.77 |
| 28~20 | 12.0 | 11.4 | −0.64 |
| 20~4 | 61.6 | 58.1 | 3.47 |

*Difference = Contents of Second Batch − Contents of First Batch

The major portion of particles (>60 (w/w) %) was large size particles (Tyler Mesh No. 20-4). However, the particle size distribution for two different batches was not significantly different (See FIG. 49).

The composition of the corn stover was analyzed by using it as a lignocellulosic substrate. Its major components were cellulose, hemicellulose, lignin, and ash. In this experiment, the corn stover compositions in the first and second batches were analyzed and the variations between two batches were identified.

Untreated, washed corn stover was analyzed for moisture content using NREL Standard Procedure No. 001. Klason lignin content and acid soluble lignin content were analyzed by NREL Standard Procedures No. 003 and 004, respectively. Ash content was obtained by NREL Standard Procedure No. 005. Protein and mineral contents were determined by Department of Soil and Forage, Texas A&M University using standard protocols.

The amounts cellulose and hemicellulose were estimated by subtracting the above contents from 100%.

Lignin (Klason+acid-soluble lignin), protein, and other minor contents were identical in both batches of corn stover. However, the ash content of the second batch corn stover was 2.45% lower than that of the first batch corn stover (See Table 3).

The lignin content of untreated, washed corn stover was not affected by washing because almost same lignin content was found in raw corn stover (20.9%). But the ash content of raw corn stover decreased from 11.1% to 6.89% after washing alone.

TABLE 3

Composition analysis of untreated, washed corn stover in batches one and two

| Batch No. | Holo-cellulose* (%) | Lignin (%) | | | Ash (%) | Protein (%) | Others** (%) |
|---|---|---|---|---|---|---|---|
| | | Klason | Acid-soluble | Total | | | |
| 1 | 70.4 | 18.5 | 2.49 | 21.0 | 6.89 | 0.78 | 0.95 |
| 2 | 73.6 | 17.8 | 2.43 | 20.3 | 4.44 | 0.71 | 0.98 |
| 2 − 1*** | 3.21 | −0.65 | −0.06 | −0.71 | −2.45 | −0.07 | 0.03 |

*Holocellulose = Cellulose + Hemicellulose
**Others = Ca + P + K + Mg + Na + Zn + Cu + Fe + Mn
***2 − 1 = (Second batch − First batch) contents The two batches of corn stover were pretreated with lime for 16 weeks at 25, 35, 45, and 55° C. Both non-oxidative and oxidative conditions were employed. The loading rates of lime and distilled water were 0.5 g $Ca(OH)_2$/g dry biomass and 10 mL water/g dry biomass, respectively. The lime-treated corn stover was harvested from each reactor at 0, 1, 2, 4, 8, and 16 weeks.

Under the non-oxidative lime treatment conditions, less than 0.1 g $Ca(OH)_2$/g dry biomass was consumed during 16 weeks. Lime consumption did not depend on temperature. After 16 weeks, the total protein content decreased from 0.78% in the untreated corn stover to 0.30% in the non-oxidatively treated corn stover and 0.23% in the oxidatively treated corn stover at 55° C. On the other hand, in the oxidative lime treatment, much more than 0.1 g $Ca(OH)_2$/g dry biomass was consumed. Lime consumption depended on temperature and thus the maximum amounts of lime consumed oxidatively were 0.11, 0.14, 0.28, and 0.42 g $Ca(OH)_2$/g dry biomass at 25, 35, 45, and 55° C., respectively.

Temperature and oxygen without lime addition did not significantly affect the delignification of corn stover. Higher temperature in oxidative conditions with lime provided the highest amounts of delignification. This oxidative delignification followed first-order reaction kinetics.

Untreated and treated corn stover were hydrolyzed by cellulase and cellobiase. The loading rate of cellulase was 0, 1, 5, 10, 20, and 60 FPU/g dry biomass and that of cellobiase was 28.5 CBU/g dry biomass. The 3-day enzyme digestibility of the biomass increased dramatically during the first few weeks in lime pretreatment. Oxidative lime pretreatment rendered the corn stover more digestible than the non-oxidative lime pretreatment. For instance, at a low cellulase loading of 1 FPU/g dry biomass, the 3-day enzyme digestibility of oxidatively treated corn stover was improved more than 77-109 mg equivalent glucose/g dry biomass compared with the non-oxidative treatment for 16 weeks.

Four sets of packed bed PVC columns (D×L=1 inch×17 inch) were constructed for lime-pretreatment reactions at 25 (room temperature), 35, 45, and 55° C. Each set was composed of two subsets, one with and one without aeration. The total number of columns for each subset was 10 in order to be analyzed at five different run-times. Two columns were harvested simultaneously at each run-time: 0, 1, 2, 4, 8, and 16 weeks. The treated biomass harvested from one of two columns was used to analyze mass balance, lime consumption, lignin, protein and minerals, crystallinity, and acetyl group. The treated biomass from the other column was dedicated to enzyme hydrolysis studies. Three sets of columns with water jackets were operated at three different temperatures, 35, 45, and 55° C., using the water heating and circulating system.

The water heating and circulating system included two parts: temperature controller and water circulator. The temperature controller contained a temperature controller (1/16 DIN, OMEGA), a thermocouple (KTSS-18G-18, OMEGA), a heating element (1.5 kW, 120 V), a solid-state relay (RSSDN-25A, Idec Co.), fuses (12.5 A and 0.25 A), and a main switch. The water circulator included a centrifugal pump (¾ HP, TEEL), a water tank (8 gal, Nalgene), a manifold having one input and 20 output fittings, and return pipelines.

Air supplied by the Carter-Mattil compressor was preheated and saturated in the cylinder within the water tank and then distributed to each column by the air-manifold having one input and 10 output fittings. Compressed nitrogen gas (Plaxair Co.) was used for the non-oxidation condition and supplied to each column by the $N_2$-manifold after preheating and saturation.

FIG. 47 is a schematic diagram of one subset of the jacketed reactor system for non-oxidative lime pretreatment. FIG. 48 shows the apparatus for oxidative lime pretreatment.

The solid content of the initial dried corn stover (iDCS) was determined as described in NREL Standard Procedure No. 001. Corn stover was treated with lime, $Ca(OH)_2$, within each column. Each column was disassembled according to the time schedule and the analytical experiments were performed on the pretreated biomass.

Some small portions of biomass were retained inside of column reactor when the column was disassembled to harvest the treated or the untreated wet biomasses. Mass recovery yield was determined for this step and considered in the mass balance.

In order to examine mass recovery, after 1-hour incubation at ambient temperature, reactors were disassembled. The wet biomass and lime mixture was harvested carefully from each reactor to 1-L centrifuge bottle using sufficient amounts of distilled water. Without washing, lime concentration was directly determined by a neutralizing titration method with 5-N HCl in a manner similar to that in Example 2. The titrated biomass was then centrifuged at 4,000 rpm for 15 minutes. Biomass slurry was obtained on the pre-weighed filter paper after filtration using aspirator. The solid content of the final dried corn stover (fDCS) was determined as described in NREL Standard Procedure No. 001.

Mass recovery yield was 95.59±1.92% as shown in Table 4. Lime recovery yield was 94.43±0.62%.

TABLE 4

Mass recovery yield after column disassembly

| Trial | Raw (g) | Solid (%) | iDCS (g) | fDCS (g) | Recovery |
|---|---|---|---|---|---|
| 1 | 15.66 | 95.70 | 14.99 | 14.24 | 95.04% |
| 2 | 15.66 | 95.70 | 14.99 | 14.09 | 94.00% |
| 3 | 15.66 | 95.70 | 14.99 | 14.65 | 97.73% |
| | | Mean | | | 95.59% |
| | | STDEV | | | 1.92% |

Mass balance was determined to get the basic database in this study of lime pretreatment of corn stover Mass recovery yields were listed in Table 5.

TABLE 5

Mass balance of treated corn stover in non-oxidative and oxidative conditions

| Temp. | Time (weeks) | Non-oxidative Conditions | | | Oxidative Conditions | | |
|---|---|---|---|---|---|---|---|
| | | iDCS (g) | fDCS (g) | Recovery | iDCS (g) | fDCS (g) | Recovery |
| 25° C. | 1 | 15.14 | 12.96 | 85.63% | 15.14 | 12.45 | 82.26% |
| | 2 | 15.14 | 12.62 | 83.35% | 15.14 | 12.29 | 81.16% |
| | 4 | 15.14 | 12.45 | 82.21% | 15.14 | 12.04 | 79.52% |
| | 8 | 15.14 | 12.22 | 80.74% | 15.14 | 11.77 | 77.77% |
| | 15 | 15.06 | 11.61 | 77.09% | 15.06 | 10.73 | 71.23% |
| 35° C. | 1 | 15.02 | 12.50 | 83.21% | 15.02 | 12.19 | 81.15% |
| | 2 | 15.12 | 12.14 | 80.27% | 15.12 | 11.44 | 75.66% |
| | 4 | 15.12 | 11.99 | 79.28% | 15.12 | 11.71 | 77.44% |
| | 8 | 14.96 | 11.64 | 77.80% | 14.96 | 11.40 | 76.22% |
| | 12 | 14.96 | 11.62 | 77.68% | 14.96 | 11.06 | 73.92% |
| | 16 | 14.96 | 11.73 | 78.38% | 14.96 | 11.35 | 75.85% |
| 45° C. | 1 | 15.02 | 12.17 | 81.04% | 15.02 | 11.79 | 78.46% |
| | 2 | 14.86 | 11.97 | 80.60% | 14.86 | 11.48 | 77.29% |
| | 4 | 14.86 | 11.72 | 78.87% | 14.86 | 11.38 | 76.62% |
| | 8 | 14.93 | 11.54 | 77.30% | 14.93 | 11.55 | 77.33% |
| | 12 | 14.93 | 12.00 | 80.34% | 14.93 | 11.13 | 74.53% |
| | 16 | 14.93 | 11.56 | 77.43% | 14.93 | 11.59 | 77.63% |
| 55° C. | 1 | 15.09 | 11.74 | 77.83% | 15.09 | 11.53 | 76.40% |
| | 2 | 15.05 | 11.55 | 76.70% | 15.05 | 11.37 | 75.53% |
| | 4 | 15.09 | 11.56 | 76.63% | 15.09 | 12.48 | 82.69% |
| | 6 | 15.09 | 11.45 | 75.92% | 15.09 | 11.59 | 76.79% |
| | 8 | 15.05 | 11.23 | 74.63% | 15.05 | 12.54 | 83.29% |
| | 12 | 15.05 | 11.06 | 73.45% | 15.05 | 11.57 | 76.84% |
| | 16 | 14.97 | 11.44 | 76.39% | 14.97 | 11.48 | 76.69% |

The amount of lime consumed during the pretreatment was determined by titrating with 5-N HCl solution at pH 7.0. Certified 5-N HCl was used to determine the remaining amounts of lime in the treated biomass mixture. The lime-treated biomass was harvested from the column reactor and transferred into a 1-L centrifuge bottle. 5-N HCl was gradually added to neutralize the treated biomass mixture until pH 7.0. During the titration, the pH of the mixture was measured while agitating continuously. The amount of 5-N HCl used for titration was recorded to estimate the amount of lime unreacted in the mixture (R) using the following formula:

$$R(g) = Mw \times \Delta V \times N2 \times 1000$$

where Mw=molecular weight of lime.
ΔV=volume of 5-N HCl titrated, and
N=normality concentration of HCl.

The amount of lime consumed (C) during the pretreatment was estimated from the following mass balance for lime: C (g)=the initial amount of lime in reactor–R.

Figure 51:
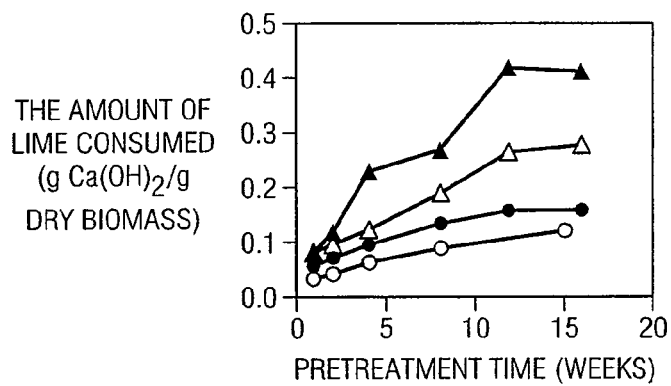
FIG. 51 presents profiles of lime consumption for oxidative pretreatment at 25, 35, 45 and 55° C. according to an embodiment of the present invention.

During the non-oxidative lime treatment, less than 0.1 g $Ca(OH)_2$/g dry biomass was consumed during 16 weeks. The maximum amount of lime consumed was 0.07 g $Ca(OH)_2$/g dry biomass. Lime consumption did not depend on temperature in non-oxidative pretreatment conditions (FIG. 50). Under oxidative lime pretreatment conditions, however, the amount of lime consumed did depend on temperature. Lime consumption increased as temperature increased (FIG. 51). The maximum amounts of lime consumed oxidatively were 0.11, 0.14, 0.28, and 0.42 g $Ca(OH)_2$/g dry biomass at 25, 35, 45, and 55° C., respectively.

As shown above, the lignin content of corn stover was not affected with washing only. Additional experiments similar to those above also showed that lignin content was not substantially affected absent addition of lime. Non-oxidative treatment without lime was studied to identify the temperature effect on delignification. Oxidative treatment without lime was studied to identify the combined effect of temperature and aeration on delignification. Oxidative research conditions were achieved by aerating at 25 and 55° C.

15.0 g of corn stover and 150.0 mL of distilled water were loaded in column reactors, which were operated as the same procedure described above for pretreatment, except that no lime was added.

Non-oxidative and oxidative conditions without lime were achieved by purging nitrogen gas and air during the 10-week operation at 25 and 55° C., respectively.

The treated corn stover was used to determine Klason, acid-soluble, and total lignin contents. Analytical methods were described in NREL Standard Procedures No. 003 and 004.

There were no significant effects of temperature or aeration on delignification as shown in Table 6.

TABLE 6

Comparison of lignin contents of untreated corn stover both non-oxidative and oxidative conditions without lime addition*

| | | Lignin Content | | |
|---|---|---|---|---|
| Condition | Temperature (° C.) | Klason (%) | Acid-soluble (%) | Total (%) |
| Non- | 25 | 19.34 | 2.00 | 21.34 |
| oxidative | 55 | 19.90 | 1.64 | 21.54 |
| Oxidative | 25 | 19.27 | 2.01 | 21.28 |
| | 55 | 18.72 | 1.55 | 20.27 |
| Control** | — | 18.50 | 2.49 | 21.00 |

*The first batch of corn stover from the lime experiments above was used in this study. Operation time was 10 weeks
**The first batch of untreated, washed corn stover.

Delignification of corn stover was achieved by lime treatment. Non-oxidative treatment with lime was used to identify the temperature effect on delignification. Oxidative treatment with lime was used to identify the combined effect of temperature and aeration on delignification.

Corn stover was treated with lime in non-oxdiative and oxidative conditions. The treated corn stover was used to determine Klason, acid-soluble, and total lignin contents. Analytical methods were described in NREL Standard Procedures No. 003 and 004.

Figure 52:
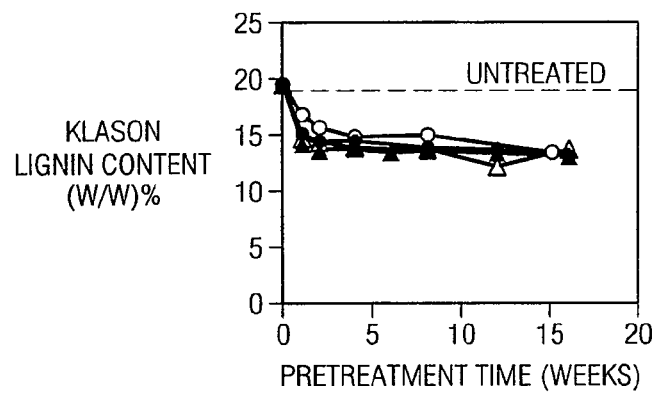
FIG. 52 presents profiles of Klason lignin content in non-oxidative lime pretreatment at 25, 35, 45 and 55° C. according to an embodiment of the present invention.

After non-oxidative lime pretreatment, Klason lignin content decreased from 19.6% down to 13%. Delignification occurred significantly within the first 2 weeks of treatment but did not depend on temperature after around 4 weeks (FIG. 52).

Figure 53:
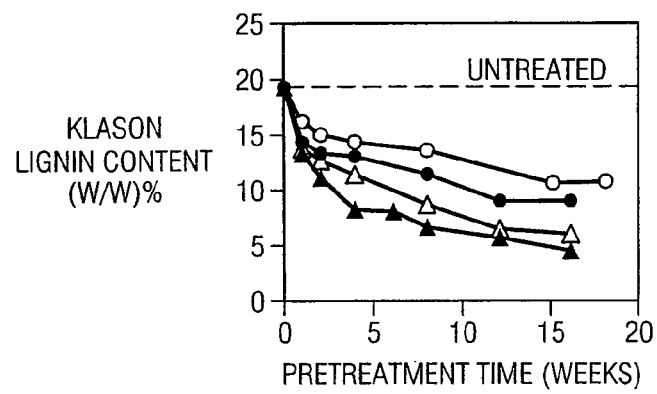
FIG. 53 presents profiles of Klason lignin content in oxidative lime pretreatment at 25, 35, 45 and 55° C. according to an embodiment of the present invention.

In contrast, during oxidative pretreatment, the Klason lignin content decreased significantly throughout the entire treatment time. Delignification depended on temperature at this condition (FIG. 53).

Figure 54:
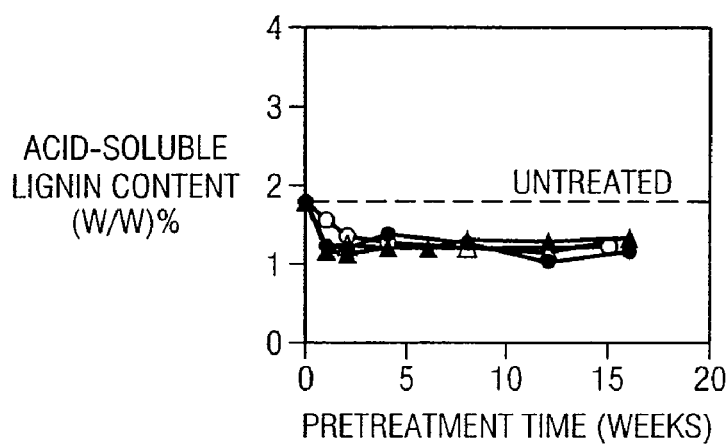
FIG. 54 presents profiles of acid-soluble lignin content in non-oxidative lime pretreatment at 25, 35, 45 and 55° C. according to an embodiment of the present invention.

During the non-oxidative lime pretreatment, acid-soluble lignin content decreased from 1.8% to 1.2%. The reduction tendency of acid-soluble lignin was similar to that of Klason lignin (FIG. 54).

Figure 55:
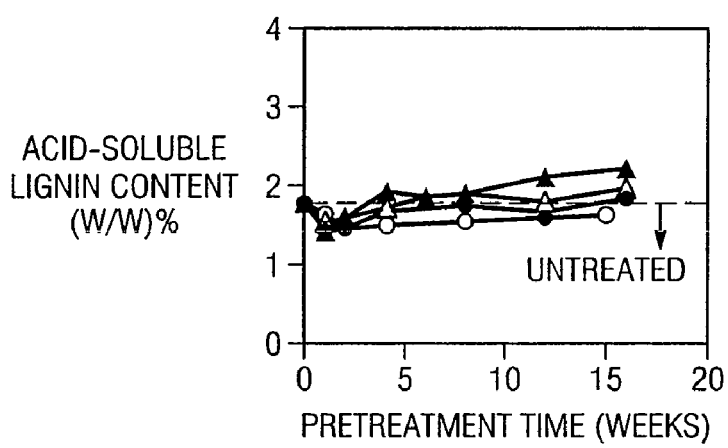
FIG. 55 presents profiles of acid-soluble lignin content in oxidative lime pretreatment at 25, 35, 45 and 55° C. according to an embodiment of the present invention.

Under oxidative pretreatment, however, acid-soluble lignin contents started to decrease for the first 2 weeks, but gradually recovered after 2 weeks, even though the increase was relatively small compared with Klason lignin contents. The recovering rate of acid-soluble lignin also increased as temperature increased as shown in FIG. 55.

During the 16-week lime pretreatment, non-oxidative delignification removed up to 29.1, 32.9, 29.2, and 31.8% of lignin at 25, 35, 45, and 55° C., respectively. Oxidative delignification, however, removed up to 40.9, 48.0, 61.8, and 67.7% of lignin at 25, 35, 45, and 55° C., respectively during the same period.

Delignification by oxidative lime pretreatment followed first-order kinetics expressed as following rate equation:

$$\frac{dL}{dt} = k \cdot L$$

where L=total lignin content (=Klason lignin+acid soluble lignin), and
k=rate constant of delignification.
The integrated form of this equation is $$\ln L = -k \cdot t + \ln L_0$$

where $L_o$=Initial total lignin content.

The result of regression analysis with SAS for data obtained in this example is summarized in Table 7. Fitting results for the data of non-oxidative lime pretreatment were poor, but the data for oxidative treatment fit the integrated equation very well.

Figure 56:
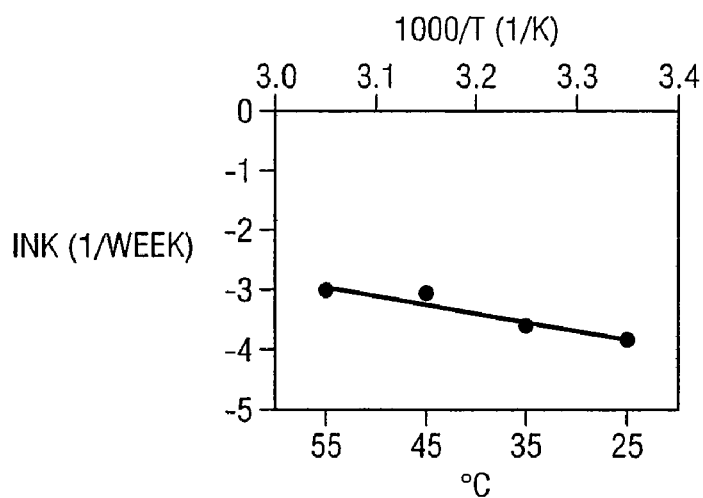
FIG. 56 presents an Arrhenius plot lnk versus 1000/T for the oxidative delignification of corn stover according to an embodiment of the present invention.

The delignification rate constant (k) is a function of temperature, thus it can be expressed in the Arrhenius equation as follows:

$$k = k_o \exp(-E_a/RT)$$

where $k_o$=pre-exponential factor (1/week)
$E_a$=activation energy (Joule/mol),
R=ideal gas constant, 8.314 Joule/(mol·K),
T=absolute temperature (K),
The Arrhenius plot is shown in FIG. 56.
From the data listed in Table 7 and FIG. 56, $k_o$ and $E_a$ were determined.
Activation energy ($E_a$) for oxidative delignification was determined as follows:
Slope=$-E_a/R$=−2973.5 K,
thus $E_a$=(2973.5)×(8.314)=24.72 kJ/mol.

Figure 57:
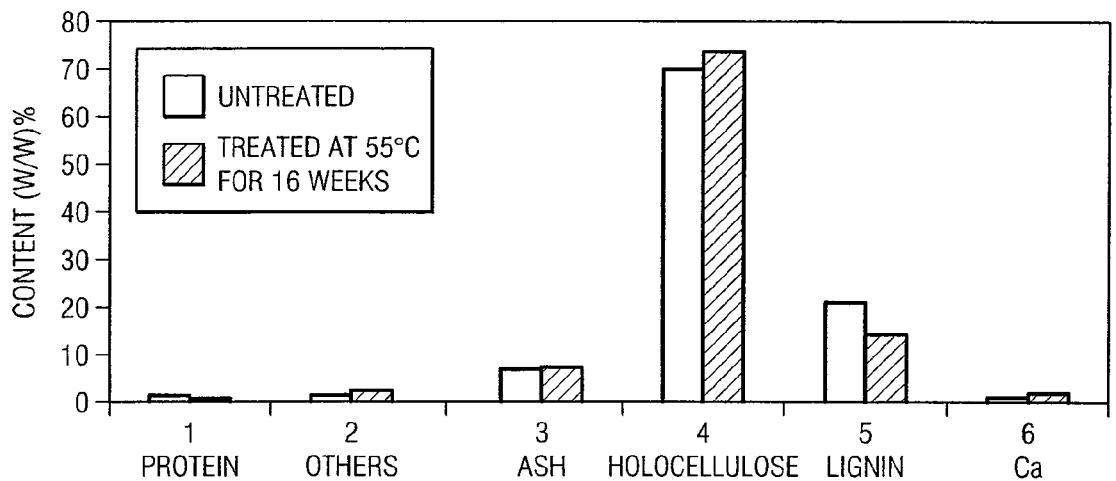
FIG. 57 presents composition changes caused by non-oxidative lime pretreatment at 55° C. according to an embodiment of the present invention.

Lime treatment increased the holocellulose content due to the reduction of lignin content (FIG. 57).

To compare their digestibilities, untreated and treated corn stovers were hydrolyzed to monosaccharides by cellulase and cellobiase. The digestibilities of corn stover treated with non-oxidative and oxidative lime at 25, 35, 45, and 55° C. were also determined.

Substrates were the untreated, washed, the non-oxidatively treated, and the oxidatively treated corn stovers. Enzyme reaction procedures were standard procedures described in Example 3.

Figure 58:
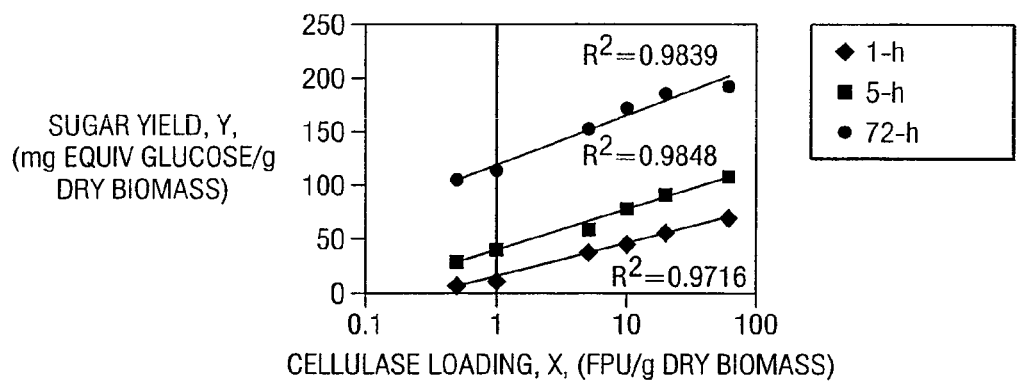
FIG. 58 presents sugar yield profiles of untreated corn stover according to cellulose loading rate at the enzyme reaction times: 1, 5, and 72 hours.

The 3-day enzyme digestibility of untreated corn stover was 153 and 193 mg equiv. glucose/g dry biomass at 5 and 60 FPU/g dry biomass of enzyme (cellulose) loading, respectively. Enzyme hydrolysis profiles (FIG. 58) fit well to the following equation:

$$Y = A \cdot \ln(X) + B$$

where Y=sugar yield (mg equivalent glucose/g dry biomass),
X=cellulase loading rate (FPU/g dry biomass), and
A and B are empirical constants.

Figure 59:
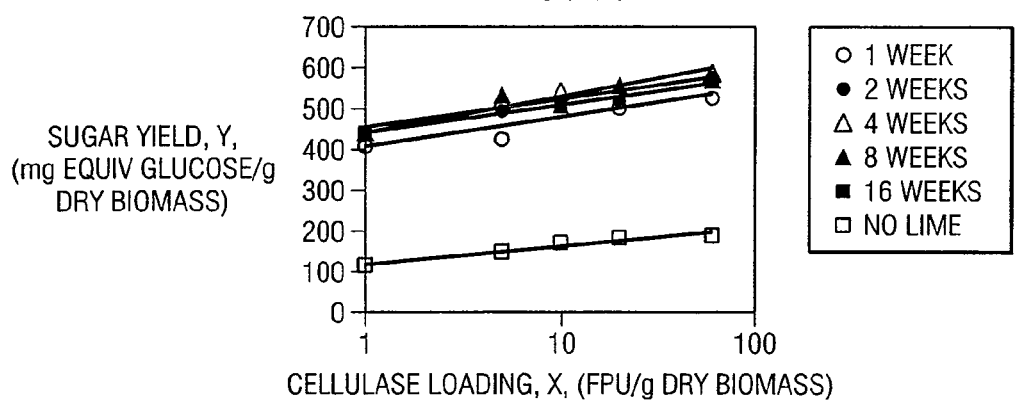
FIG. 59 presents the 3-day enzyme digestibility profiles of treated corn stover in non-oxidative conditions for 16 weeks at 25, 35, 45 and 55° C. according to an embodiment of the present invention.

During the 16-week non-oxidative lime pretreatment, 3-day enzyme digestibility increased 3-fold more than of the untreated corn stover over the entire range of cellulase concentrations (FIG. 59).

Figure 60:
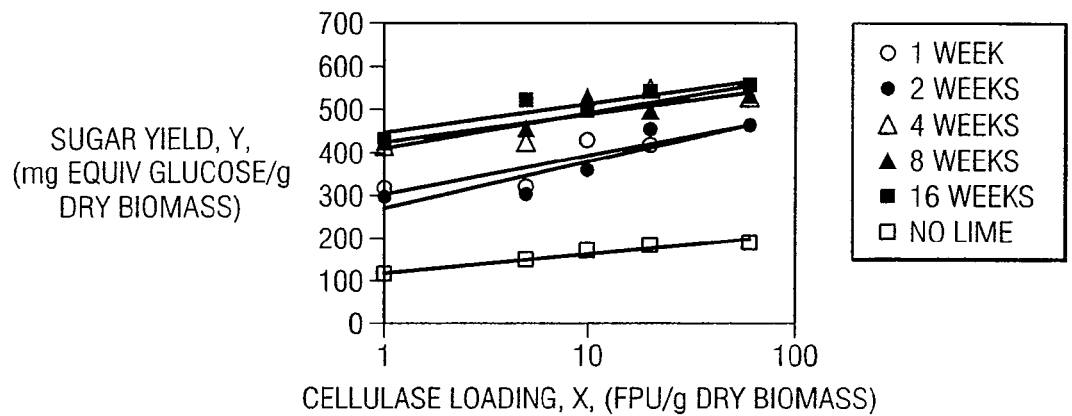
FIG. 60 presents the 3-day enzyme digestibility profiles of treated corn stover in non-oxidative conditions for 1, 2, 4, 8 and 16 weeks at 55° C. according to an embodiment of the present invention.

Under most conditions, 3-day enzyme digestibility increased dramatically for the first few weeks and increased continuously for the remaining treatment. Interestingly, the 3-day enzyme digestibility of non-oxidatively treated corn stover at 55° C. reached the maximum after a 4-week lime pretreatment (FIG. 60).

Figure 61:
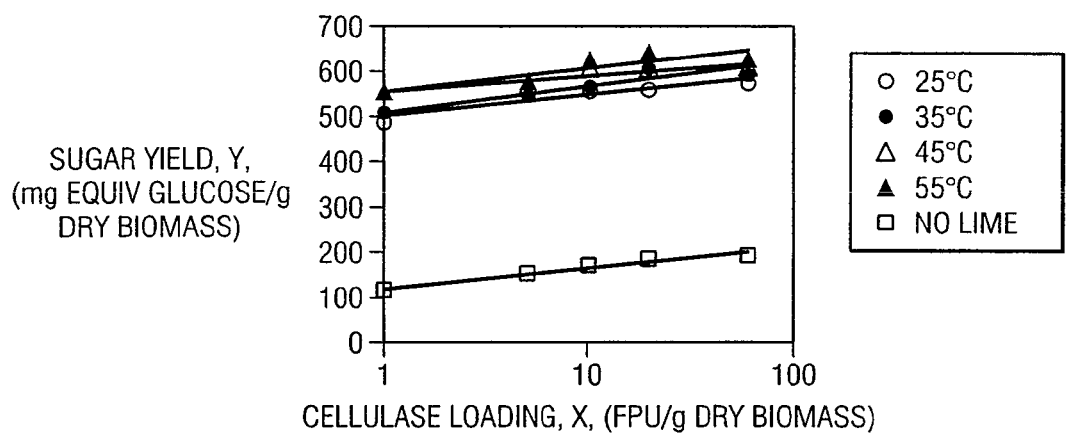
FIG. 61 presents the 3-day enzyme digestibility profiles of treated corn stover in oxidative conditions for 16 weeks at 25, 35, 45 and 55° C. according to an embodiment of the present invention.
Figure 62A:
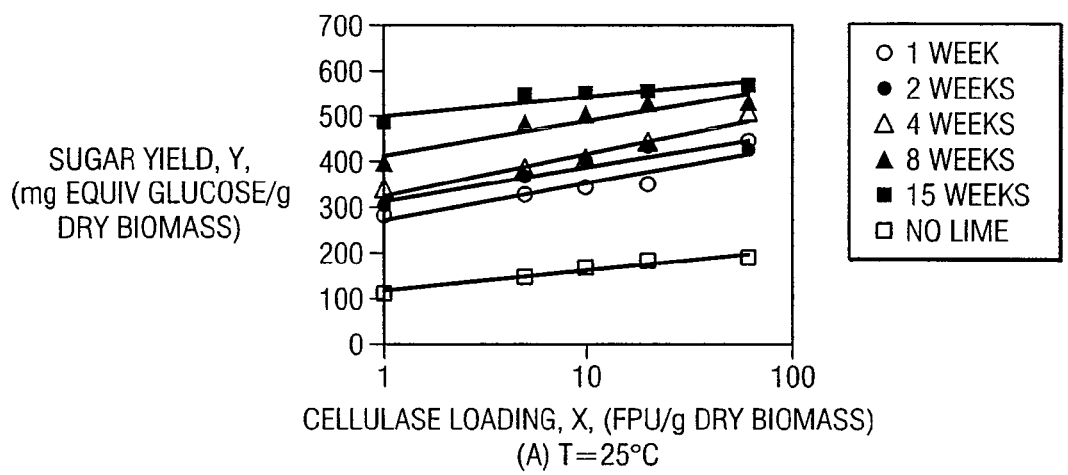
FIG. 62 presents the 3-day enzyme digestibility profiles of treated corn stover in oxidative conditions for 1, 2, 4, 8, 12 and 16 weeks at (a) 25, (b) 35, (c) 45 and (d)55° C. according to an embodiment of the present invention.
Figure 62B:
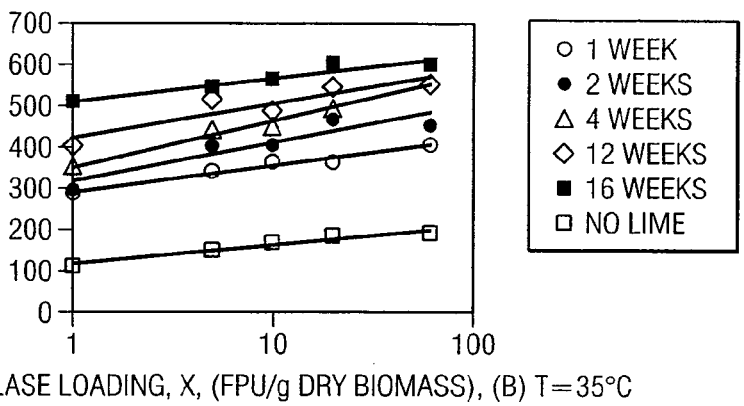
Figure 62C:
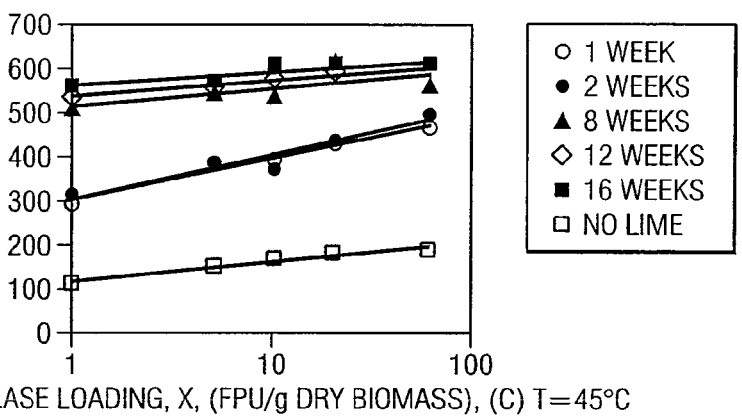
Figure 62D:
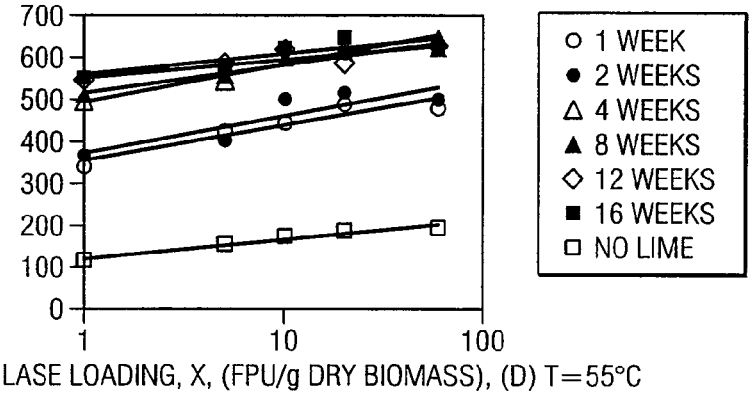
Figure 63A:
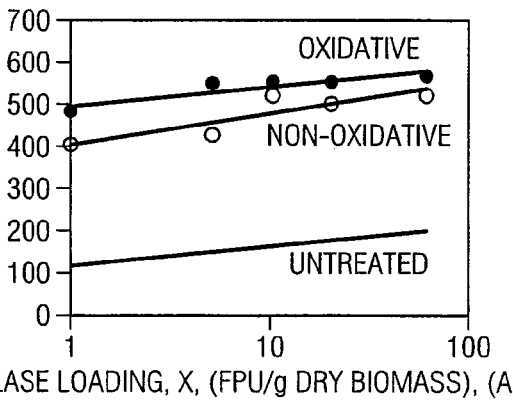
FIG. 63 presents a comparison of the 3-day enzyme digestibility profiles between non-oxidative and oxidative treated corn stover for 16 weeks at (a) 25, (b) 35, (c) 45 and (d) 55° C. according to an embodiment of the present invention.
Figure 63B:
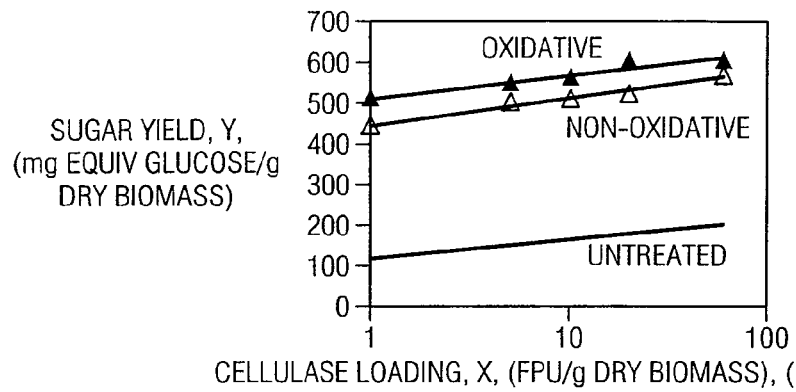
Figure 63C:
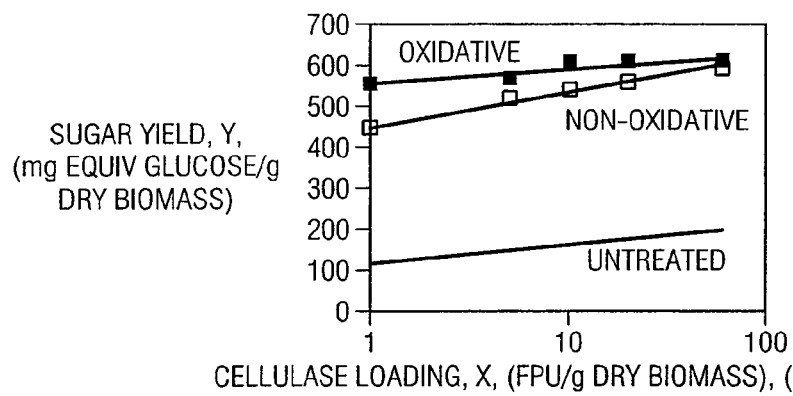
Figure 63D:
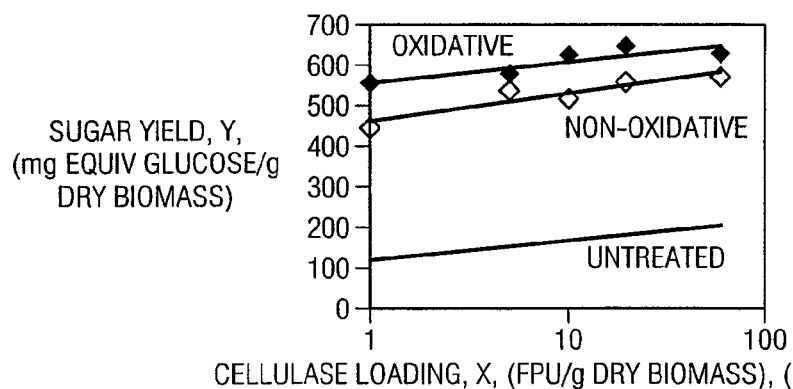

During the 16-week oxidative lime pretreatment, the 3-day enzyme digestibility increased by more 15-123 mg equivalent glucose/g dry biomass than that of the 16-week non-oxidative lime pretreatment (FIG. 63 and Table 6.1). The improvement of 3-day enzyme digestibility from non-oxidative values to oxidative values depended on the cellulase loading: the lower the cellulase loading, the greater improvement of 3-day enzyme digestibility. The 3-day enzyme digestibility profiles of the 16-week oxidatively treated corn stover were similar to those of the non-oxidatively treated corn stover (FIG. 61).

In contrast, oxidative lime treatment shortened the pretreatment time required to obtain maximal 3-day enzyme digestibility at higher treatment temperatures (See FIG. 62 and Table 6.2).

For example, using a cellulase loading only of 1 FPU/g dry biomass, the 3-day enzyme digestibility of the oxidatively treated corn stover improved more than 77-109 mg equivalent glucose/g dry biomass compared with the non-oxidative treatment for 16 weeks (FIG. 63).

TABLE 7

Results of linear regression analysis for delignification data of lime pretreatement.

| Condition for Lime Pretreatment | Temp. (° C.) | $\ln L_0$ (g lignin/g dry biomass) | $L_0$ (g lignin/g dry biomass) | k (week$^{-1}$) | Regression Coefficient ($R^2$) |
|---|---|---|---|---|---|
| Non-oxidative | 25 | −1.7336 | 0.1767 | 0.0099 | 0.7919 |
| | 35 | −1.8177 | 0.1624 | 0.0075 | 0.8830 |
| | 45 | −1.8259 | 0.1611 | 0.0077 | 0.4484 |
| | 55 | −1.8720 | 0.1538 | 0.0032 | 0.5595 |
| Oxidative | 25 | −1.7421 | 0.1752 | 0.0214 | 0.9516 |
| | 35 | −1.8380 | 0.1591 | 0.0270 | 0.9225 |
| | 45 | −1.8668 | 0.1546 | 0.0460 | 0.9661 |
| | 55 | −1.9959 | 0.1359 | 0.0483 | 0.9026 |

It is likely that enhanced 3-day enzyme digestibility mainly results from lime reaction, which is boosted by the presence of oxygen. Higher temperatures are more favorable because they result in greater deliginification, which results in the faster digestion of biomass.

TABLE 8

Differences* in 3-day enzyme digestibility between non-oxidative and oxidative treated corn stover treated for 16 weeks

| Temp. | Cellulose Loading (FPU/g dry biomass) | | | | |
|---|---|---|---|---|---|
| (° C.) | 1 | 5 | 10 | 20 | 60 |
| 25 | 77.24 | 123.10 | 31.54 | 51.88 | 44.65 |
| 35 | 67.18 | 44.26. | 55.44 | 83.13 | 32.54 |
| 45 | 121.71 | 46.40 | 64.83 | 46.43 | 15.35 |
| 55 | 109.10 | 42.75 | 109.64 | 87.23 | 57.93 |

*Difference = Data of oxidative treatment − Data of non-oxidative treatment

TABLE 9

The minimal oxidative treatment time (t500) required to obtain greater than 500 mg equivalent glucose/g dry biomass of 3-d enzyme digestibility at 1 FPU/g dry biomass of cellulase loading (Based on the data of FIG. 63)

| Temperature (° C.) | $t_{500}$ (weeks) |
|---|---|
| 25 | >16 |
| 35 | 16 |
| 45 | 8 |
| 55 | 4 |

Figure 64:
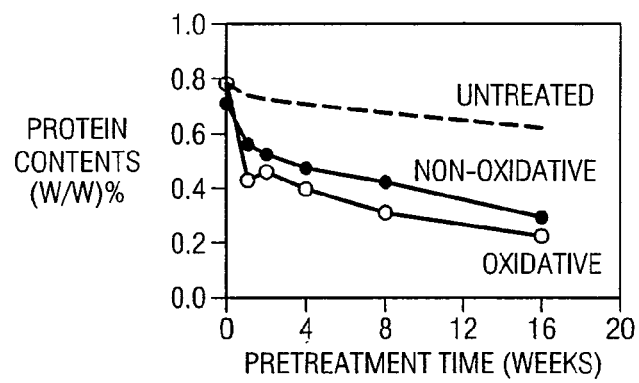
FIG. 64 presents profiles of protein content reduction during non-oxidative and oxidative pretreatments at 55° C. according to an embodiment of the present invention.

Total protein content of the oxidatively treated corn stover was much lower than that of the non-oxidatively treated corn stover as shown in FIG. 64

The invention claimed is:

1. A method of biomass pretreatment comprising:
   (a) adding an alkali to biomass with lignin content to produce a mixture;
   (b) maintaining the mixture at a temperature between approximately 25° C. and 100° C. at ambient pressure;
   (c) circulating water intermittently through the mixture during step (b);
   (d) fermenting the biomass; and
   (e) collecting carboxylate salts from the mixture.

2. The method of claim 1, further comprising maintaining the mixture for a time period of at least approximately 4 weeks.

3. The method of claim 1, further comprising maintaining the mixture for a time period of between approximately 4 and 16 weeks.

4. The method of claim 1, further comprising selecting the duration of step (b) based on the temperature in step (b).

5. The method of claim 1, wherein the biomass comprises lignocellulosic biomass.

6. The method of claim 1, wherein the biomass comprises agricultural waste.

7. The method of claim 1, wherein the biomass is selected from the group consisting of: bagasse, corn stover and combinations thereof.

8. The method of claim 1, further comprising circulating oxygen enriched air or pure oxygen through the mixture during step (b).

9. The method of claim 1, wherein the alkali comprises lime.

10. The method of claim 1, wherein the alkali comprises calcium oxide.

11. The method of claim 9, further comprising adding approximately 0.5 grams of lime per gram of biomass to produce the mixture.

12. The method of claim 9, further comprising adding approximately 0.1 to 0.5 grams of lime per gram of biomass to produce the mixture.

13. The method of claim 9, further comprising adding lime to the biomass in an amount between approximately 10% and 30% of biomass by weight.

14. The method of claim 1, further comprising adding calcium carbonate to the mixture.

15. The method of claim 1, further comprising maintaining the mixture at a temperature between approximately 25° C. and 90° C.

16. The method of claim 1, further comprising maintaining the mixture at a temperature between approximately 25° C. and 57° C.

17. The method of claim 1, further comprising selecting the temperature in step (b) based on the partial pressure of water at the selected temperature.

18. The method of claim 1, further comprising increasing the enzyme digestibility of the biomass.

19. The method of claim 1, further comprising producing pulp.

20. The method of claim 19, further comprising producing pulp suitable for paper or cardboard production.

21. The method of claim 1, further comprising reducing the lignin content of the biomass.

22. The method of claim 21, further comprising reducing lignin content by at least approximately 98%.

23. The method of claim 21, further comprising reducing lignin content by at least approximately 90%.

24. The method of claim 21, further comprising reducing lignin content by at least approximately 29%.

25. The method of claim 21, further comprising reducing lignin content by at least approximately 40%.

26. The method of claim 21, further comprising reducing lignin content by at least approximately 67%.

27. The method of claim 21, further comprising reducing lignin content by alkaline oxidation.

28. The method of claim 1, further comprising adding an inoculum to the mixture.

29. The method of claim 1, wherein maintaining the mixture occurs at ambient pressure, and wherein the temperature is between 25° C. and 95° C.

30. A method for producing enzymatically digestible biomass comprising:
   (a) adding lime to biomass with lignin content to produce a mixture;
   (b) maintaining the mixture at a temperature between approximately 25° C. and 55° C. at ambient pressure for a time period of at least approximately 4 to 16 weeks;
   (c) circulating water intermittently through the mixture during step (b);
   (d) fermenting the biomass; and
   (e) collecting carboxylate salts from the mixture.

31. The method of claim 30, further comprising circulating air or oxygen enriched air or pure oxygen through the mixture during step (b).

32. The method of claim 30, further comprising reducing the lignin content of the biomass by at least approximately 67%.

33. The method of claim 30, further comprising reducing the lignin content of the biomass by at least approximately 32%.

34. A method for producing pulp comprising:
(a) adding lime to biomass with lignin content to produce a mixture;
(b) maintaining the mixture at a temperature between approximately 45° C. and 55° C. at ambient pressure for a time period of approximately 10 weeks;
(c) circulating water intermittently through the mixture during step (b);
(d) fermenting the biomass; and
(e) collecting carboxylate salts from the mixture.

35. The method of claim 34, further comprising circulating air or oxygen enriched air through the mixture during step (b).

36. The method of claim 34, further comprising reducing the lignin content of the biomass by at least approximately 90%.

37. The method of claim 34, further comprising reducing the lignin content of the biomass by at least approximately 40%.

38. The method of claim 34, further comprising producing paper or cardboard from the biomass.

\* \* \* \* \*